US008361742B2

(12) United States Patent
Martin et al.

(10) Patent No.: US 8,361,742 B2
(45) Date of Patent: *Jan. 29, 2013

(54) **METHOD FOR DETECTING *CANDIDA* ON SKIN**

(75) Inventors: Stephanie M. Martin, Woodstock, GA (US); Andrew M. Long, III, Appleton, WI (US); John Gavin MacDonald, Decatur, GA (US); Jason Lye, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 63 days.

This patent is subject to a terminal disclaimer.

(21) Appl. No.: 12/843,922

(22) Filed: Jul. 27, 2010

(65) Prior Publication Data

US 2010/0291670 A1 Nov. 18, 2010

Related U.S. Application Data

(62) Division of application No. 11/513,500, filed on Aug. 31, 2006, now Pat. No. 7,763,442.

(51) Int. Cl.
*C12Q 1/22* (2006.01)
*C12Q 1/02* (2006.01)
(52) U.S. Cl. .................. 435/31; 435/29; 264/78; 436/1
(58) Field of Classification Search ........................ None
See application file for complete search history.

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,368,549 A | 2/1968 | Barr et al. | |
| 3,494,821 A | 2/1970 | Evans | |
| 3,502,538 A | 3/1970 | Peterson | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,918,433 A | 11/1975 | Fuisz | |
| 4,100,324 A | 7/1978 | Anderson et al. | |
| 4,144,370 A | 3/1979 | Boulton | |
| 4,340,563 A | 7/1982 | Appel et al. | |
| 4,556,636 A | 12/1985 | Belly et al. | |
| 4,578,359 A | 3/1986 | Oksman et al. | |
| 5,057,361 A | 10/1991 | Sayovitz et al. | |
| 5,181,905 A | 1/1993 | Flam | |
| 5,217,444 A | 6/1993 | Schoenfeld | |
| 5,284,703 A | 2/1994 | Everhart et al. | |
| 5,350,624 A | 9/1994 | Georger et al. | |
| 5,382,400 A | 1/1995 | Pike et al. | |
| 5,449,612 A | 9/1995 | Lepargneur et al. | |
| 5,468,236 A | 11/1995 | Everhart et al. | |
| 5,540,332 A | 7/1996 | Kopacz et al. | |
| 5,667,635 A | 9/1997 | Win et al. | |
| 5,681,380 A | 10/1997 | Nohr et al. | |
| 5,744,321 A | 4/1998 | Harewood | |
| 5,785,179 A | 7/1998 | Buczwinski et al. | |
| 5,888,524 A | 3/1999 | Cole | |
| 5,910,421 A | 6/1999 | Small, Jr. et al. | |
| 5,964,351 A | 10/1999 | Zander | |
| 6,028,018 A | 2/2000 | Amundson et al. | |
| 6,030,331 A | 2/2000 | Zander | |
| 6,060,256 A | 5/2000 | Everhart et al. | |
| 6,090,541 A | 7/2000 | Wicks et al. | |
| 6,158,614 A | 12/2000 | Haines et al. | |
| 6,197,574 B1 | 3/2001 | Miyamoto et al. | |
| 6,207,596 B1 | 3/2001 | Rourke et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,315,864 B2 | 11/2001 | Anderson et al. | |
| 6,368,558 B1 | 4/2002 | Suslick et al. | |
| 6,387,651 B1 | 5/2002 | Bochner et al. | |
| 6,433,244 B1 | 8/2002 | Roe et al. | |
| 6,436,651 B1 | 8/2002 | Everhart et al. | |
| 6,440,437 B1 | 8/2002 | Krzysik et al. | |
| 6,479,727 B1 | 11/2002 | Roe | |
| 6,501,002 B1 | 12/2002 | Roe et al. | |
| 6,542,379 B1 | 4/2003 | Lauffer et al. | |

(Continued)

FOREIGN PATENT DOCUMENTS

EP 1 143246 A1 10/2001
EP 1 527888 A2 5/2005

(Continued)

OTHER PUBLICATIONS

Janzen et al., "Colorimetric Sensor Arrays for Volatile Organic Compounds," *Anal. Chem.*, vol. 76, 2006, pp. 3591-3600.

(Continued)

*Primary Examiner* — Lisa J Hobbs
(74) *Attorney, Agent, or Firm* — Dority & Manning, P.A.

(57) ABSTRACT

A method and system for rapidly detecting *Candida* on the skin of a host, such as an infant with diaper rash, is provided. The method includes contacting a dermal sample with a colorant that exhibits a certain spectral response (e.g., color change) in the presence of *Candida*. For example, the colorant may change from a first color to a second color, from colorless to a color, or from a color to colorless. The colorant is typically capable of differentiating between *Candida* (e.g., *Candida albicans*) and other microorganisms commonly associated with diaper rash, such as *S. aureus* and *E. coli*. Thus, when a dermal sample is placed into contact with the colorant, the color change may simply be observed to determine whether the infection is caused by *Candida*. If the color change occurs to a certain extent (e.g., from yellow to bright red), it may be determined that the test sample contains *Candida*. Likewise, if a color change occurs to a lesser extent (e.g., from yellow to faint orange) or not at all, it may be determined that the dermal sample contains other microorganisms (e.g., *S. aureus* or *E. coli*), no infection is present, or that the infection is simply due to other causes. Regardless, it will become readily apparent whether or not treatment for *Candida* is needed.

9 Claims, 2 Drawing Sheets

U.S. PATENT DOCUMENTS

| | | |
|---|---|---|
| 6,551,791 B1 | 4/2003 | Small et al. |
| 6,589,761 B1 | 7/2003 | Freadman et al. |
| 6,645,930 B1 | 11/2003 | Wallis et al. |
| 6,713,660 B1 | 3/2004 | Roe et al. |
| 6,951,730 B2 | 10/2005 | Small et al. |
| 6,967,084 B2 | 11/2005 | Small et al. |
| 7,531,319 B2 | 5/2009 | Martin |
| 2002/0177828 A1 | 11/2002 | Batich et al. |
| 2003/0119202 A1 | 6/2003 | Kaylor et al. |
| 2003/0143112 A1 | 7/2003 | Suslick et al. |
| 2004/0014161 A1 | 1/2004 | Janes et al. |
| 2004/0029171 A1 | 2/2004 | Wagner et al. |
| 2004/0113801 A1 | 6/2004 | Gustafson et al. |
| 2004/0172000 A1 | 9/2004 | Roe et al. |
| 2005/0084464 A1 | 4/2005 | McGrath et al. |
| 2005/0101841 A9 | 5/2005 | Kaylor et al. |
| 2005/0112085 A1 | 5/2005 | MacDonald et al. |
| 2005/0124072 A1 | 6/2005 | Boga et al. |
| 2005/0130253 A1 | 6/2005 | Lye et al. |
| 2005/0136238 A1 | 6/2005 | Lindsay et al. |
| 2005/0160543 A1 | 7/2005 | Catalfamo et al. |
| 2005/0250089 A1 | 11/2005 | Chandrapati et al. |
| 2005/0250168 A1 | 11/2005 | Gonzalez et al. |
| 2005/0250169 A1 | 11/2005 | Gonzalez et al. |
| 2006/0000043 A1 | 1/2006 | Jou-Chen et al. |
| 2006/0003649 A1 | 1/2006 | Runge et al. |
| 2006/0062689 A1 | 3/2006 | Kirollos et al. |
| 2006/0114754 A1 | 6/2006 | MacDonald et al. |
| 2006/0134613 A1 | 6/2006 | Martin et al. |
| 2006/0134728 A1 | 6/2006 | MacDonald et al. |
| 2006/0210970 A1 | 9/2006 | Debad et al. |
| 2009/0111088 A1 | 4/2009 | Martin et al. |
| 2009/0221061 A1 | 9/2009 | Martin et al. |

FOREIGN PATENT DOCUMENTS

| | | |
|---|---|---|
| GB | 1987 2178847 | 2/1987 |
| JP | 2005 253412 A | 9/2005 |
| WO | WO 89 05093 | 6/1989 |
| WO | WO 00 55359 A1 | 9/2000 |
| WO | WO 01 71318 A1 | 9/2001 |
| WO | WO 01 85081 A1 | 11/2001 |
| WO | WO 02 30478 A2 | 4/2002 |
| WO | WO 02 30478 A3 | 4/2002 |
| WO | WO 2005 042771 A2 | 5/2005 |
| WO | WO 2005 059162 A2 | 6/2005 |
| WO | WO 2006 105193 A2 | 10/2006 |
| WO | WO 2006 105193 A3 | 10/2006 |
| WO | WO 2007 009047 A2 | 1/2007 |
| WO | WO 2007 009047 A3 | 1/2007 |
| WO | WO 2007 027899 A1 | 3/2007 |

OTHER PUBLICATIONS

Ponder, Jennifer B., "Colorimetic Sensor Array: Do I See What You Smell," Final Seminar, 515, "Inorganic Seminar" (under the Guidance of K. S. Suslick and in collaboration with J. R. Carey, K. I. Hulkower, C. K. Ingison, A Sen and A. E. Wittrig, Dept. of Chemistry and Microbiology, U. Illinois, Urbana, May 8, 2006.

Todar, K., "The Normal Bacterial Flora of Humans," http://www.tesxtbookofbacteriology.net/normalflora.html, Aug. 26, 2011.

Microgen Bioproducts Newsletter, No. 17, 2004.

F. Cost—*Pocket Guide to Digital Printing*, Delmar Publishers, pp. 144-145, Jul. 31, 1996.

*Color and Constitution of Organic Molecules*—Academic Press, (1976) p. 11.

Koidl et al.—*Rapid Diagnosis of Adenoviral Keratoconjunctivitis by a Fully Automated Molecular Assay*, Opthalmology, vol. 112, No. 9 Sep. 2005, pp. 1521.e1-1521.e8.

Bochner et al., *Phenotype MicroArrays for High-Throughput Phenotypic Testing and Assay of Gene Function*, Genome Research, pp. 1246-1255 (2001 by Cold Spring Harbor Laboratory Press ISSN 088-9051/01).

Search Report and Written Opinion for PCT/IB2007/052872 dated Mar. 5, 2008.

METHOD FOR DETECTING *CANDIDA* ON SKIN

RELATED APPLICATIONS

The present application is a divisional of U.S. application Ser. No. 11/513,500, filed on Aug. 31, 2006, which is incorporated herein in its entirety by reference thereto.

BACKGROUND OF THE INVENTION

"Diaper rash" (also referred to as diaper dermatitis or incontinent dermatitis) is a common form of irritation and inflammation affecting both infants and incontinent adults within the skin regions normally covered by a diaper (e.g., rectal and genital areas). Diaper rash may develop when skin is exposed to prolonged contact with urine or feces, which increases skirt pH and contributes to the breakdown of the stratum corneum. Although diaper rash is usually resolved in a short time period, the skin still becomes susceptible to more serious secondary infections once the stratum corneum is damaged. One of the more problematic secondary infections associated with diaper rash is "yeast infection", which is typically caused by *Candida albicans*. Under the conditions that result in diaper rash, for instance, the normally unicellular yeast-like form of *Candida albicans* can convert into an invasive, multicellular filamentous form. *Candida* infection may result in painful swelling and become difficult to resolve. In severely immune compromised patients, *Candida albicans* infection may even spread throughout the body and cause systemic infections. It is believed that some of the symptoms of *Candida* infections may be minimized or eliminated with early treatment. Currently, however, no convenient system exists for rapidly alerting a caregiver or user of a secondary *Candida* infection on the skin.

As such, a need currently exists for a technique of rapidly and simply detecting the presence of *Candida* infection on skin.

SUMMARY OF THE INVENTION

In accordance with one embodiment of the present invention, a method for detecting *Candida* on the skin of a host is disclosed. The method comprises contacting a dermal sample with a colorant that produces a visually observable spectral response (e.g., color change) in the presence of *Candida*; detecting the spectral response; and correlating the detected spectral response to the presence of *Candida* in the dermal sample.

In accordance with another embodiment of the present invention, a system for detecting a secondary infection associated with diaper rash is disclosed. The system comprises a solid support applied with a colorant. The colorant produces a first spectral response in the presence of *Candida albicans*, a second spectral response in the presence of *Staphylococcus aureus*, and a third spectral response in the presence of *Escherichia coli*. The first spectral response is visually distinctive from the second and third spectral responses.

In accordance with yet another embodiment of the present invention, a wipe for detecting a secondary infection associated with diaper rash is disclosed. The wipe comprises a colorant that produces a first spectral response in the presence of *Candida albicans*, a second spectral response in the presence of *Staphylococcus aureus*, and a third spectral response in the presence of *Escherichia coli*. The first spectral response is visually distinctive from the second and third spectral responses.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1A:
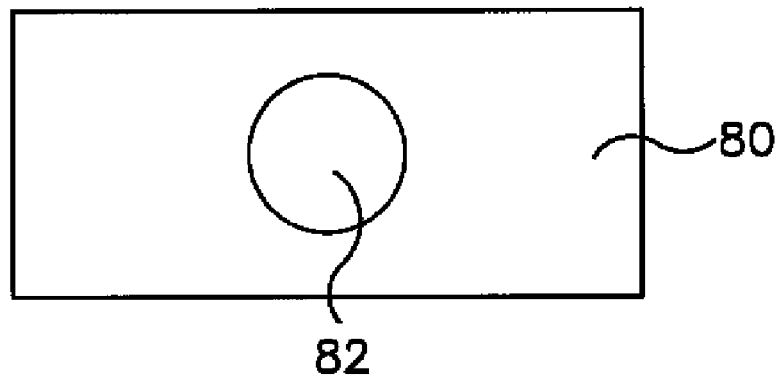
FIG. 1 is a perspective view of an exemplary wipe of the present invention before contact with a dermal sample (FIG. 1A) and after contact with a sample infected with *Candida albicans* (FIG. 1B)

Repeat use of reference characters in the present specification and drawings is intended to represent same or analogous features or elements of the invention.

DETAILED DESCRIPTION OF REPRESENTATIVE EMBODIMENTS

Definitions

As used herein, the term "*Candida*" refers to a genus of the Fungi kingdom that includes, for instance, the species *Candida albicans, Candida dubliniensis, Candida glabrata, Candida guilliermondii, Candida kefyr, Candida krusei, Candida lusitaniae, Candida parapsilosis, Candida tropicalis*, and *Candida utilis*.

As used herein, the term "dermal sample" generally refers to the skin of a host (e.g., any animal, preferably a human) and/or a biological material obtained directly and/or indirectly from the skin, such as from discharge, tissue, etc. The test sample may optionally be pretreated before testing, such as by filtration, precipitation, dilution, distillation, mixing, concentration, inactivation of interfering components, the addition of reagents, lysing, etc.

As used herein the term "nonwoven web" generally refers to a web having a structure of individual fibers or threads which are interlaid, but not in an identifiable manner as in a knitted fabric. Examples of suitable nonwoven webs include, but are not limited to, meltblown webs, spunbond webs, carded webs, airlaid webs, etc. The basis weight of the nonwoven web may vary, such as from about 5 grams per square meter ("gsm") to 120 gsm, in some embodiments from about 10 gsm to about 70 gsm, and in some embodiments, from about 15 gsm to about 35 gsm.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. Nos. 4,340,563 to Appel, et al., 3,692,618 to Dorschner, et al., 3,802,817 to Matsuki, et al., 3,338,992 to Kinney, 3,341,394 to Kinney, 3,502,763 to Hartman, 3,502,538 to Levy, 3,542,615 to Dobo, et al., and 5,382,400 to Pike, et al., which are incorporated herein in their entirety by reference thereto for all purposes. Spunbond fibers are generally not tacky when they are deposited onto a collecting surface. Spunbond fibers may sometimes have diameters less than about 40 microns, and are often between about 5 to about 20 microns.

As used herein, the term "carded web" refers to a web made from staple fibers that are sent through a combing or carding unit, which separates or breaks apart and aligns the staple fibers in the machine direction to form a generally machine direction-oriented fibrous nonwoven web. Such fibers are usually obtained in bales and placed in an opener/blender or picker, which separates the fibers prior to the carding unit. Once formed, the web may then be bonded by one or more known methods.

As used herein, the term "airlaid web" refers to a web made from bundles of fibers having typical lengths ranging from about 3 to about 19 millimeters (mm). The fibers are separated, entrained in an air supply, and then deposited onto a forming surface, usually with the assistance of a vacuum supply. Once formed, the web is then bonded by one or more known methods.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a method and system for rapidly detecting *Candida* on the skin of a host, such as an infant with diaper rash. The method includes contacting a dermal sample with a colorant that exhibits a certain spectral response (e.g., color change) in the presence of *Candida*. For example, the colorant may change from a first color to a second color, from colorless to a color, or from a color to colorless. The colorant is typically capable of differentiating between *Candida* (e.g., *Candida albicans*) and other microorganisms commonly associated with diaper rash, such as *S. aureus* and *E. coli*. Thus, when a dermal sample is placed into contact with the colorant, the color change may simply be observed to determine whether the infection is caused by *Candida*. If the color change occurs to a certain extent (e.g., from yellow to bright red), it may be determined that the test sample contains *Candida*. Likewise, if a color change occurs to a lesser extent (e.g., from yellow to faint orange) or not at all, it may be determined that the dermal sample contains other microorganisms (e.g., *S. aureus* or *E. coli*), no infection is present, or that the infection is simply due to other causes. Regardless, it will become readily apparent whether or not treatment for *Candida* is needed.

One particularly suitable class of colorants that may undergo a detectable color change in the presence of *Candida* is pH-sensitive colorants. Namely, pH-sensitive colorants can detect a change in the pH of the growth medium of the microorganism. Because the acidic/basic shift may vary for different microorganisms, pH-sensitive colorants may be selected that are tuned for the desired pH transition. Certain *Candida* species (e.g., *Candida albicans*) for instance, are believed to produce metabolites or other byproducts that alter the pH of the growth medium to about 6.6. Thus, pH-sensitive colorants that undergo a change in pH at or near this level may be used in the present invention. Phenol Red (i.e., phenolsulfonephthalein), for example, may be particularly suitable in that it exhibits a transition from yellow to red over a pH range of about 6.6 to 8.0.

Other phthalein colorants, however, may also be used in the present invention to indicate the presence of *Candida*. Derivatives of Phenol Red, for instance, may be employed, such as those substituted with chloro, bromo, methyl, sodium carboxylate, carboxylic acid, hydroxyl and amine functional groups. Exemplary substituted Phenol Red compounds include, for instance, Chlorophenol Red, Metacresol Purple (meta-cresolsulfonephthalein), Cresol Red (ortho-cresolsulfonephthalein), Pyrocatecol Violet (pyrocatecolsulfonephthalein), Chlorophenol Red (3',3"-dichlorophenolsulfonephthalein), Xylenol Blue (the sodium salt of para-xylenolsulfonephthalein), Xylenol Orange, Mordant Blue 3 (C.I. 43820), 3,4,5,6-tetrabromophenolsulfonephthalein, Bromoxylenol Blue, Bromophenol Blue (3',3", 5',5"-tetrabromophenolsulfonephthalein), Bromochlorophenol Blue (the sodium salt of dibromo-5',5"-dichlorophenolsulfonephthalein), Bromocresol Purple (5',5"-dibromo-ortho-cresolsulfonephthalein), Bromocresol Green (3',3", 5',5"-tetrabromo-ortho-cresolsulfonephthalein), and so forth. Still other suitable phthalein colorants are well known in the art, and may include Bromothymol Blue, Thymol Blue, Bromocresol Purple, thymolphthalein, and phenolphthalein (a common component of universal indicators). For example, Chlorophenol Red exhibits a transition from yellow to red over a pH range of about 4.8 to 6.4; Bromothymol Blue exhibits a transition from yellow to blue over a pH range of about 6.0 to 7.6; thymolphthalein exhibits a transition from colorless to blue over a pH range of about 9.4 to 10.6; phenolphthalein exhibits a transition from colorless to pink over a pH range of about 8.2 to 10.0; Thymol Blue exhibits a first transition from red to yellow over a pH range of about 1.2 to 2.8 and a second transition from yellow to pH over a pH range of 8.0 to 9.6; Bromophenol Blue exhibits a transition from yellow to violet over a pH range of about 3.0 to 4.6; Bromocresol Green exhibits a transition from yellow to blue over a pH range of about 3.8 to 5.4; and Bromocresol Purple exhibits a transition from yellow to violet over a pH of about 5.2 to 6.8.

Hydroxyanthraquinones constitute another suitable class of pH-sensitive colorants for use in the present invention. Hydroxyanthraquinones have the following general structure:

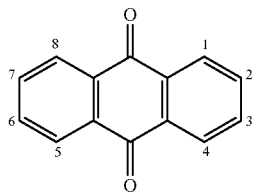 [SMILES: O=C1c2ccccc2C(=O)c2ccccc21]

The numbers 1-8 shown in the general formula represent a location on the fused ring structure at which substitution of a functional group may occur. For hydroxyanthraquinones, at least one of the functional groups is or contains a hydroxy (—OH) group. Other examples of functional groups that may be substituted on the fused ring structure include halogen groups (e.g., chlorine or bromine groups), sulfonyl groups (e.g., sulfonic acid salts), alkyl groups, benzyl groups, amino groups (e.g., primary, secondary, tertiary, or quaternary amines), carboxy groups, cyano groups, phosphorous groups, etc. Some suitable hydroxyanthraquinones that may be used in the present invention, Mordant Red 11 (Alizarin), Mordant Red 3 (Alizarin Red S), Alizarin Yellow R, Alizarin Complexone, Mordant Black 13 (Alizarin Blue Black B), Mordant Violet 5 (Alizarin Violet 3R), Alizarin Yellow GG, Natural Red 4 (carminic acid), amino-4-hydroxyanthraquinone, Emodin, Nuclear Fast Red, Natural Red 16 (Purpurin), Quinalizarin, and so forth. For instance, carminic acid exhibits a first transition from orange to red over a pH range of about 3.0 to 5.5 and a second transition from red to purple over a pH range of about 5.5 to 7.0. Alizarin Yellow R, on the other hand, exhibits a transition from yellow to orange-red over a pH range of about 10.1 to 12.0.

Yet another suitable class of pH-sensitive colorants that may be employed is aromatic azo compounds having the general structure:

wherein, $R_1$ is an aromatic group;

$R_2$ is selected from the group consisting of aliphatic and aromatic groups; and X and Y are independently selected from the group consisting of hydrogen, halides, —$NO_2$, —$NH_2$, aryl groups, alkyl groups, alkoxy groups, sulfonate groups, —$SO_3H$, —OH, —COH, —COOH, halides, etc. Also suitable are azo derivatives, such as azoxy compounds (X—$R_1$—N=NO—$R_2$—Y) or hydrazo compounds (X—$R_1$—NH—NH—$R_2$—Y). Particular examples of such azo compounds (or derivatives thereof) include Methyl Violet, Methyl Yellow, Methyl Orange, Methyl Red, and Methyl Green. For instance, Methyl Violet undergoes a transition from yellow to blue-violet at a pH range of about 0 to 1.6, Methyl Yellow undergoes a transition from red to yellow at a pH range of about 2.9 to 4.0, Methyl Orange undergoes a transition from red to yellow at a pH range of about 3.1 to 4.4, and Methyl Red undergoes a transition from red to yellow at a pH range of about 4.2 to 6.3.

Arylmethanes (e.g., diarylmethanes and triarylmethanes) constitute still another class of suitable pH-sensitive colorants for use in the present invention. Triarylmethane leuco bases, for example, have the following general structure:

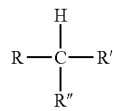

wherein R, R', and R'' are independently selected from substituted and unsubstituted aryl groups, such as phenyl, naphthyl, anthracenyl, etc. The aryl groups may be substituted with functional groups, such as amino, hydroxyl, carbonyl, carboxyl, sulfonic, alkyl, and/or other known functional groups. Examples of such triarylmethane leuco bases include Leucomalachite Green, Pararosaniline Base, Crystal Violet Lactone, Crystal Violet Leuco, Crystal Violet, CI Basic Violet 1, CI Basic Violet 2, CI Basic Blue, CI Victoria Blue, N-benzoyl leuco-methylene, etc. Likewise suitable diarylmethane leuco bases may include 4,4'-bis (dimethylamino) benzhydrol (also known as "Michler's hydrol"), Michler's hydrol leucobenzotriazole, Michler's hydrol leucomorpholine, Michler's hydrol leucobenzenesulfonamide, etc. In one particular embodiment, the colorant is Leucomalachite Green Carbinol (Solvent Green 1) or an analog thereof, which is normally colorless and has the following structure:

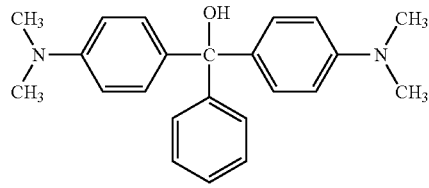

Under acidic conditions, one or more free amino groups of the Leucomalachite Green Carbinol form may be protonated to form Malachite Green (also known as Aniline Green, Basic Green 4, Diamond Green B, or Victoria Green B), which has the following structure:

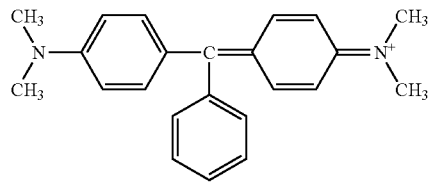

Malachite Green typically exhibits a transition from yellow to blue-green over a pH range 0.2 to 1.8. Above a pH of about 1.8, malachite green turns a deep green color.

Still other suitable pH-sensitive colorants that may be employed include Congo Red, Litmus (azolitmin), Methylene Blue, Neutral Red, Acid Fuchsin, Indigo Carmine, Brilliant Green, Picric acid, Metanil Yellow, m-Cresol Purple, Quinaldine Red, Tropaeolin OO, 2,6-dinitrophenol, Phloxine B, 2,4-dinitrophenol, 4-dimethylaminoazobenzene, 2,5-dinitrophenol, 1-Naphthyl Red, Chlorophenol Red, Hematoxylin, 4-nitrophenol, nitrazine yellow, 3-nitrophenol, Alkali Blue, Epsilon Blue, Nile Blue A, universal indicators, and so forth. For instance, Congo Red undergoes a transition from blue to red at a pH range of about 3.0 to 5.2, Litmus undergoes a transition from red to blue at a pH range of about 4.5 to 8.3, and Neutral Red undergoes a transition from red to yellow at a pH range of about 11.4 to 13.0.

In addition to pH, other mechanisms may also be wholly or partially responsible for inducing a color change in the colorant. For example, *Candida* may produce low molecular weight iron-complexing compounds in growth media, which are known as "siderophores." Metal complexing colorants may thus be employed in some embodiments of the present invention that undergo a color change in the presence of siderophores. One particularly suitable class of metal complexing colorants are aromatic azo compounds, such as Eriochrome Black T, Eriochrome Blue SE, Eriochrome Blue Black B, Eriochrome Cyanine R, Xylenol Orange, Chrome Azurol S, carminic acid, etc. Still other suitable metal complexing colorants may include Alizarin Complexone, Alizarin S, Arsenazo III, Aurintricarboxylic acid, 2,2'-Bipyidine, Bromopyrogallol Red, Calcon (Eriochrom Blue Black R), Calconcarboxylic acid, Chromotropic acid, disodium salt, Cuprizone, 5-(4-Dimethylamino-benzylidene)rhodanine, Dimethylglyoxime, 1,5-Diphenylcarbazide, Dithizone, Fluorescein Complexone, Hematoxylin, 8-Hydroxyquinoline, 2-Mercaptobenzothiazole, Methylthymol Blue, Murexide, 1-Nitroso-2-naphthol, 2-Nitroso-1-naphthol, Nitroso-R-salt, 1,10-Phenanthroline, Phenylfluorone, Phthalein Purple, 1-(2-Pyridylazo)-naphthol, 4-(2-Pyridylazo)resorcinol, Pyrogallol Red, Sulfonazo III, 5-Sulfosalicylic acid, 4-(2-Thiazolylazo)resorcinol, Thorin, Thymolthalexon, Tiron, Tolurnr-3,4-dithiol, Zincon, and so forth. It should be noted that one or more of the pH-sensitive colorants referenced above may also be classified as metal complexing colorants.

Although the above-referenced colorants are classified based on their mechanism of color change (e.g., pH sensitive, metal complexing, etc.), it should be understood that the present invention is not limited to any particular mechanism for the color change. Even when a pH-sensitive colorant is employed, for instance, other mechanisms may actually be wholly or partially responsible for the color change of the colorant. For example, redox reactions between the colorant and microorganism may contribute to the color change.

As stated above, colorants may be employed in the present invention that differentiate between the presence of *Candida* and other microorganisms commonly associated with diaper rash, such as *E. coli* and *S. aureus*. However, the method is by no means limited to the detection of *Candida*. In fact, additional colorants may also be employed in the present invention that are capable of detecting the presence of other microorganisms, such as bacteria. Several relevant bacterial groups that may be detected in the present invention include, for instance, gram negative rods (e.g., Entereobacteria); gram negative curved rods (e.g., vibious, *Heliobacter, Campylobacter*, etc.); gram negative cocci (e.g., *Neisseria*); gram positive rods (e.g., *Bacillus, Clostridium*, etc.); gram positive cocci (e.g., *Staphylococcus, Streptococcus*, etc.); obligate intracellular parasites (e.g., Ricckettsia and *Chlamydia*); acid fast rods (e.g., *Myobacterium, Nocardia*, etc.); spirochetes (e.g., *Treponema, Borellia*, etc.); and mycoplasmas (i.e., tiny bacteria that lack a cell wall). Particularly relevant bacteria include *E. coli* (gram negative rod), *Klebsiella pneumonia* (gram negative rod), *Streptococcus* (gram positive cocci), *Salmonella choleraesuis* (gram negative rod), *Staphyloccus aureus* (gram positive cocci), and *P. aeruginosa* (gram negative rod).

The colorants employed for detecting bacteria may be capable of independently differentiating bacteria, or simply provide a color change indicative of the presence of a broad spectrum of bacteria. Solvatochromatic colorants, for instance, are believed to exhibit a detectable color change in the presence of a broad spectrum of bacteria. Although solvatochromatic colorants may also undergo a color change in the presence of *Candida* microorganisms, it is generally believed to be to a lesser extent. Various suitable solvatochromatic colorants that are suitable for use in the present invention are described in U.S. Patent Application Publication No. 2006/0134728 to MacDonald, et al., which is incorporated herein in its entirety by reference thereto for all purposes. For example, merocyanine colorants (e.g., mono-, di-, and tri-merocyanines) are one example of a type of solvatochromatic colorant that may be employed in the present invention. Merocyanine colorants, such as merocyanine 540, fall within the donor-simple acceptor colorant classification of Griffiths as discussed in "Colour and Constitution of Organic Molecules" Academic Press, London (1976). More specifically, merocyanine colorants have a basic nucleus and acidic nucleus separated by a conjugated chain having an even number of methine carbons. Such colorants possess a carbonyl group that acts as an electron acceptor moiety. The electron acceptor is conjugated to an electron donating group, such as a hydroxyl or amino group. The merocyanine colorants may be cyclic or acyclic (e.g., vinylalogous amides of cyclic merocyanine colorants).

Other suitable solvatochromatic colorants that may be used in the present invention include those that possess a permanent zwitterionic form. That is, these colorants have formal positive and negative charges contained within a contiguous π-electron system. Contrary to the merocyanine colorants referenced above, a neutral resonance structure cannot be drawn for such permanent zwitterionic colorants. Exemplary colorants of this class include N-phenolate betaine colorants, such as those having the following general structure:

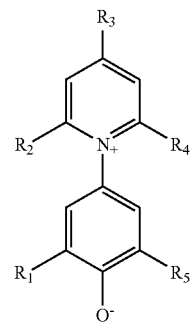

wherein $R_1$-$R_5$ are independently selected from the group consisting of hydrogen, a nitro group (e.g., nitrogen), a halogen, or a linear, branched, or cyclic $C_1$ to $C_{20}$ group (e.g., alkyl, phenyl, aryl, pyridinyl, etc.), which may be saturated or unsaturated and unsubstituted or optionally substituted at the same or at different carbon atoms with one, two or more halogen, nitro, cyano, hydroxy, alkoxy, amino, phenyl, aryl, pyridinyl, or alkylamino groups. For example, the N-phenolate betaine colorant may be 4-(2,4,6-triphenylpyridinium-1-yl)-2,6-diphenylphenolate (Reichardt's dye) having the following general structure:

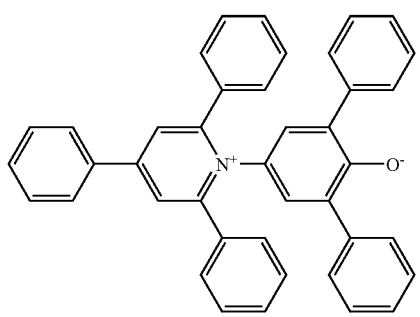 [SMILES: [O-]c1c(-c2ccccc2)cc(-[n+]2c(-c3ccccc3)cc(-c3ccccc3)cc2-c2ccccc2)cc1-c1ccccc1]

Reichardt's dye shows strong negative solvatochromism and may thus undergo a significant color change from blue to colorless in the presence of bacteria. That is, Reichardt's dye displays a shift in absorbance to a shorter wavelength and thus has visible color changes as solvent eluent strength (polarity) increases.

Regardless of the type employed, a colorant is generally applied to a solid support for subsequent contact with a dermal sample. The nature of the solid support may vary depending on the intended use, and may include materials such as films, paper, nonwoven webs, knitted fabrics, woven fabrics, foam, glass, etc. Desirably, the solid support is a wipe configured for use on skin, such as a baby wipe, adult wipe, hand wipe, face wipe, cosmetic wipe, household wipe, industrial wipe, personal cleansing wipe, cotton ball, cotton-tipped swab, and so forth. In this manner, the colorant may provide information about the presence of microorganisms in a dermal sample during and/or shortly after the normal use of the wipe. For example, the colorant may be present on a baby wipe to provide the caregiver with a rapid indication of whether a microorganism is present on the skin of a baby.

The wipe may be formed from any of a variety of materials as is well known in the art. For example, the wipe may include a nonwoven web that contains an absorbent material of sufficient wet strength and absorbency for use in the desired application. For example, the nonwoven web may include absorbent fibers formed by a variety of pulping processes, such as kraft pulp, sulfite pulp, thermomechanical pulp, etc. The pulp fibers may include softwood fibers having an average fiber length of greater than 1 mm and particularly from about 2 to 5 mm based on a length-weighted average. Such softwood fibers can include, but are not limited to, northern softwood, southern softwood, redwood, red cedar, hemlock, pine (e.g., southern pines), spruce (e.g., black spruce), combinations thereof, and so forth. Exemplary commercially available pulp fibers suitable for the present invention include those available from Kimberly-Clark Corporation under the trade designations "Longlac-19." Hardwood fibers, such as eucalyptus, maple, birch, aspen, and so forth, can also be used. In certain instances, eucalyptus fibers may be particularly desired to increase the softness of the web. Eucalyptus fibers can also enhance the brightness, increase the opacity, and change the pore structure of the web to increase its wicking ability. Moreover, if desired, secondary fibers obtained from recycled materials may be used, such as fiber pulp from sources such as, for example, newsprint, reclaimed paperboard, and office waste. Further, other absorbent fibers that may be used in the present invention, such as abaca, sabai grass, milkweed floss, pineapple leaf, cellulosic esters, cellulosic ethers, cellulosic nitrates, cellulosic acetates, cellulosic acetate butyrates, ethyl cellulose, regenerated celluloses (e.g., viscose or rayon), and so forth.

Synthetic thermoplastic fibers may also be employed in the nonwoven web, such as those formed from polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. Because many synthetic thermoplastic fibers are inherently hydrophobic (i.e., non-wettable), such fibers may optionally be rendered more hydrophilic (i.e., wettable) by treatment with a surfactant solution before, during, and/or after web formation. Other known methods for increasing wettability may also be employed, such as described in U.S. Pat. No. 5,057,361 to Sayovitz, et al., which is incorporated herein in its entirety by reference thereto for all purposes.

If desired, the nonwoven web material may be a composite that contains a combination of synthetic thermoplastic polymer fibers and absorbent fibers, such as polypropylene and pulp fibers. The relative percentages of such fibers may vary over a wide range depending on the desired characteristics of the nonwoven composite. For example, the nonwoven composite may contain from about 1 wt. % to about 60 wt. %, in some embodiments from 5 wt. % to about 50 wt. %, and in some embodiments, from about 10 wt. % to about 40 wt. % synthetic polymeric fibers. The nonwoven composite may likewise contain from about 40 wt. % to about 99 wt. %, in some embodiments from 50 wt. % to about 95 wt. %, and in some embodiments, from about 60 wt. % to about 90 wt. % absorbent fibers.

Nonwoven composites may be formed using a variety of known techniques. For example, the nonwoven composite may be a "coform material" that contains a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic and/or organic absorbent materials, treated polymeric staple fibers and so forth. Some examples of such coform materials are disclosed in U.S. Pat. Nos. 4,100,324 to Anderson, et al.; 5,284,703 to Everhart, et al.; and 5,350,624 to Georger, at al.; which are incorporated herein in their entirety by reference thereto for all purposes. Alternatively, the nonwoven composite may be formed be formed by hydraulically entangling fibers and/or filaments with high-pressure jet streams of water. Hydraulically entangled nonwoven composites of staple length fibers and continuous filaments are disclosed, for example, in U.S. Pat. Nos. 3,494,821 to Evans and 4,144,370 to Bouolton, which are incorporated herein in their entirety by reference thereto for all purposes. Hydraulically entangled nonwoven composites of a continuous filament nonwoven web and pulp fibers are disclosed, for example, in U.S. Pat. Nos. 5,284,703 to Everhart, et al. and 6,315,864 to Anderson, at al., which are incorporated herein in their entirety by reference thereto for all purposes.

Regardless of the materials or processes utilized to form the wipe, the basis weight of the wipe is typically from about 20 to about 200 grams per square meter (gsm), and in some embodiments, between about 35 to about 100 gsm. Lower basis weight products may be particularly well suited for use as light duty wipes, while higher basis weight products may be better adapted for use as industrial wipes.

The wipe may assume a variety of shapes, including but not limited to, generally circular, oval, square, rectangular, or irregularly shaped. Each individual wipe may be arranged in a folded configuration and stacked one on top of the other to provide a stack of wet wipes. Such folded configurations are well known to those skilled in the art and include c-folded, z-folded, quarter-folded configurations and so forth. For example, the wipe may have an unfolded length of from about 2.0 to about 80.0 centimeters, and in some embodiments, from about 10.0 to about 25.0 centimeters. The wipes may likewise have an unfolded width of from about 2.0 to about 80.0 centimeters, and in some embodiments, from about 10.0 to about 25.0 centimeters. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing. Various suitable dispensers, containers, and systems for delivering wipes are described in U.S. Pat. Nos. 5,785,179 to Buczwinski, et al.; 5,964,351 to Zander; 6,030,331 to Zander; 6,158,614 to Haynes, et al.; 6,269,969 to Huang, et al.; 6,269,970 to Huang, et al.; and 6,273,359 to Newman, et al., which are incorporated herein in their entirety by reference thereto for all purposes.

In certain embodiments of the present invention, the wipe is a "wet wipe" in that it contains a solution for cleaning, disinfecting, sanitizing, etc. The particular wet wipe solutions are not critical and are described in more detail in U.S. Pat. Nos. 6,440,437 to Krzysik, et al.; 6,028,018 to Amundson, et al.; 5,888,524 to Cole; 5,667,635 to Win, et al.; and 5,540,332 to Kopacz, et al., which are incorporated herein in their entirety by reference thereto for all purposes. The amount of the wet wipe solution employed may depending upon the type of wipe material utilized, the type of container used to store the wipes, the nature of the cleaning formulation, and the desired end use of the wipes. Generally, each wipe contains from about 150 to about 600 wt. % and desirably from about 300 to about 500 wt. % of a wet wipe solution based on the dry weight of the wipe.

Typically, the colorant of the present invention is applied to a wipe or other solid support in the form of a composition that contains a mobile carrier. The carrier may be a liquid, gas, gel, etc., and may be selected to provide the desired performance (time for change of color, contrast between different areas, and sensitivity) of the colorant. In some embodiments, for instance, the carrier may be an aqueous solvent, such as water, as well as a non-aqueous solvent, such as glycols (e.g., propylene glycol, butylene glycol, triethylene glycol, hexylene glycol, polyethylene glycols, ethoxydiglycol, and dipropyleneglycol); alcohols (e.g., methanol, ethanol, n-propanol, and isopropanol); triglycerides; ethyl acetate; acetone; triacetin; acetonitrile, tetrahydrafuran; xylenes; formaldehydes (e.g., dimethylformamide, "DMF"); etc. Suitable techniques for applying the colorant composition to the solid support include printing, dipping, spraying, melt extruding, coating (e.g., solvent coating, powder coating, brush coating, etc.), and so forth. Upon application, the colorant composition may be dried to remove the carrier and leave a residue of the colorant for interacting with a microorganism.

Other additives may also be employed, either separately or in conjunction with a colorant composition. In one embodiment, for instance, cyclodextrins are employed that enhance the sensitivity and contrast of a colorant. While not wishing to be bound by theory, the present inventors believe that such additives may inhibit the crystallization of the colorant and thus provide a more vivid color and also enhance detection sensitivity. That is, single colorant molecules have greater sensitivity for microorganisms because each colorant molecule is free to interact with the microbial membrane. In contrast, small crystals of colorant have to first dissolve and then penetrate the membrane. Examples of suitable cyclodextrins may include, but are not limited to, hydroxypropyl-β-cyclodextrin, hydroxyethyl-β-cyclodextrin, γ-cyclodextrin, hydroxypropyl-γ-cyclodextrin, and hydroxyethyl-γ-cyclodextrin, which are commercially available from Cerestar International of Hammond, Ind.

Surfactants may also help enhance the sensitivity and contrast provided by the colorant. Particularly desired surfactants are nonionic surfactants, such as ethoxylated alkylphenols, ethoxylated and propoxylated fatty alcohols, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, acetylenic diols, and mixtures thereof. Various specific examples of suitable nonionic surfactants include, but are not limited to, methyl gluceth-10, PEG-20 methyl glucose distearate, PEG-20 methyl glucose sesquistearate, $C_{11}$-$C_{15}$ pareth-20, ceteth-8, ceteth-12, dodoxynol-12, laureth-15, PEG-20 castor oil, polysorbate 20, steareth-20, polyoxyethylene-10 cetyl ether, polyoxyethylene-10 stearyl ether, polyoxyethylene-20 cetyl ether, polyoxyethylene-10 oleyl ether, polyoxyethylene-20 oleyl ether, an ethoxylated nonylphenol, ethoxylated octylphenol, ethoxylated dodecylphenol, or ethoxylated fatty ($C_6$-$C_{22}$) alcohol, including 3 to 20 ethylene oxide moieties, polyoxyethylene-20 isohexadecyl ether, polyoxyethylene-23 glycerol laurate, polyoxy-ethylene-20 glyceryl stearate, PPG-10 methyl glucose ether, PPG-20 methyl glucose ether, polyoxyethylene-20 sorbitan monoesters, polyoxyethylene-80 castor oil, polyoxyethylene-15 tridecyl ether, polyoxy-ethylene-6 tridecyl ether, laureth-2, laureth-3, laureth-4, PEG-3 castor oil, PEG 600 dioleate, PEG 400 dioleate, and mixtures thereof. Commercially available nonionic surfactants may include the SURFYNOL® range of acetylenic diol surfactants available from Air Products and Chemicals of Allentown, Pa. and the TWEEN® range of polyoxyethylene surfactants available from Fischer Scientific of Pittsburgh, Pa.

A binder may also be employed to facilitate the immobilization of the colorant on the wipe or other solid support. For example, water-soluble organic polymers may be employed as binders, such as polysaccharides and derivatives thereof. Polysaccharides are polymers containing repeated carbohydrate units, which may be cationic, anionic, nonionic, and/or amphoteric. In one particular embodiment, the polysaccharide is a nonionic, cationic, anionic, and/or amphoteric cellulosic ether. Suitable nonionic cellulosic ethers may include, but are not limited to, alkyl cellulose ethers, such as methyl cellulose and ethyl cellulose; hydroxyalkyl cellulose ethers, such as hydroxyethyl cellulose, hydroxypropyl cellulose, hydroxypropyl hydroxybutyl cellulose, hydroxyethyl hydroxypropyl cellulose, hydroxyethyl hydroxybutyl cellulose and hydroxyethyl hydroxypropyl hydroxybutyl cellulose; alkyl hydroxyalkyl cellulose ethers, such as methyl hydroxyethyl cellulose, methyl hydroxypropyl cellulose, ethyl hydroxyethyl cellulose, ethyl hydroxypropyl cellulose, methyl ethyl hydroxyethyl cellulose and methyl ethyl hydroxypropyl cellulose; and so forth.

The colorant composition may be applied to all or only a portion of the wiper or other solid support. Suitable techniques for applying the colorant composition to the solid support include printing, dipping, spraying, melt extruding, coating (e.g., solvent coating, powder coating, brush coating, etc.), spraying, and so forth. In one embodiment, for example, the colorant composition is printed onto the support (e.g., wipe), such as in the form of indicia that conveys a certain message to the user.

A variety of printing techniques may be used for applying the colorant composition to the support, such as gravure printing, flexographic printing, screen printing, laser printing, thermal ribbon printing, piston printing, etc. In one particular embodiment, ink-jet printing techniques are employed to apply the colorant composition to the support. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system may be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically. Thus, when the sample channel is formed from a dielectric material, DOD printing techniques may be more desirable.

The colorant composition may be formed as a printing ink using any of a variety of known components and/or methods. For example, the printing ink may contain water as a carrier, and particularly deionized water. Various co-carriers may also be included in the ink, such as lactam, N-methylpyrrolidone, N-methylacetamide, N-methylmorpholine-N-oxide, N,N-dimethylacetamide, N-methyl formamide, propyleneglycol-monomethylether, tetramethylene sulfone, tripropyleneglycolmonomethylether, propylene glycol, and triethanolamine (TEA). Humectants may also be utilized, such as ethylene glycol; diethylene glycol; glycerine; polyethylene glycol 200, 300, 400, and 600; propane 1,3 diol; propyleneglycolmonomethyl ethers, such as Dowanol PM (Gallade Chemical Inc., Santa Ana, Calif.); polyhydric alcohols; or combinations thereof. Other additives may also be included to improve ink performance, such as a chelating agent to sequester metal ions that could become involved in chemical reactions over time, a corrosion inhibitor to help protect metal components of the printer or ink delivery system, and a surfactant to adjust the ink surface tension. Various other components for use in an ink, such as colorant stabilizers, photoinitiators, binders, surfactants, electrolytic salts, pH adjusters, etc., may be employed as described in U.S. Patent Nos. 5,681,380 to Nohr, et al. and 6,542,379 to Nohr, et al., which are incorporated herein in their entirety by reference thereto for all purposes.

If desired, the composition may also be applied to a strip that is subsequently adhered or otherwise attached to the solid support. For example, the strip may contain a facestock material commonly employed in the manufacture of labels, such as paper, polyester, polyethylene, polypropylene, polybutylene, polyamides, etc. An adhesive, such as a pressure-sensitive adhesive, heat-activated adhesive, hot melt adhesive, etc., may be employed on one or more surfaces of the facestock material to help adhere it to a surface of the solid support. Suitable examples of pressure-sensitive adhesives include, for instance, acrylic-based adhesives and elastomeric adhesives. In one embodiment, the pressure-sensitive adhesive is based on copolymers of acrylic acid esters (e.g., 2-ethyl hexyl acrylate) with polar co-monomers (e.g., acrylic acid). The adhesive may have a thickness in the range of from about 0.1 to about 2 mils (2.5 to 50 microns). A release liner may also be employed that contacts the adhesive prior to use. The release liner may contain any of a variety of materials known to those of skill in the art, such as a silicone-coated paper or film substrate.

The exact quantity of a colorant employed in the present invention may vary based on a variety of factors, including the sensitivity of the colorant, the presence of other additives, the desired degree of detectability (e.g., with an unaided eye), the suspected concentration of the microorganism, etc. In some cases, it is desirable to only detect the presence of *Candida* at a pathogenic concentration. For example, a *Candida* concentration of about $1 \times 10^3$ colony forming units ("CFU") per milliliter of growth media or more, in some embodiments about $1 \times 10^5$ CFU/ml or more, in some embodiments about $1 \times 10^6$ CFU/ml or more, and in some embodiments, about $1 \times 10^7$ CFU/ml or more may be considered pathogenic. It should be understood that such concentrations may correlate to a liquid sample or a non-liquid sample (e.g., skin or obtained from skin) that is cultured in a growth media. Regardless, the colorant may be employed in an amount sufficient to undergo a detectable color change in the presence of *Candida* at a desired concentration. For instance, the colorant may be applied at a concentration from about 0.1 to about 100 milligrams per milliliter of carrier, in some embodiments from about 0.5 to about 60 milligrams per milliliter of carrier, and in some embodiments, from about 1 to about 40 milligrams per milliliter of carrier. Likewise, the colorant may constitute from about 0.001 wt. % to about 20 wt. %, in some embodiments from about 0.01 wt. % to about 10 wt. %, and in some embodiments from about 0.1 wt. % to about 5 wt. % of the dry weight of the solid support.

The degree to which a colorant changes color may be determined either visually or using instrumentation. In one embodiment, color intensity is measured with an optical reader. The actual configuration and structure of the optical reader may generally vary as is readily understood by those skilled in the art. Typically, the optical reader contains an illumination source that is capable of emitting electromagnetic radiation and a detector that is capable of registering a signal (e.g., transmitted or reflected light). The illumination source may be any device known in the art that is capable of providing electromagnetic radiation, such as light in the visible or near-visible range (e.g., infrared or ultraviolet light). For example, suitable illumination sources that may be used in the present invention include, but are not limited to, light emitting diodes (LED), flashlamps, cold-cathode fluorescent lamps, electroluminescent lamps, and so forth. The illumination may be multiplexed and/or collimated. In some cases, the illumination may be pulsed to reduce any background interference. Further, illumination may be continuous or may combine continuous wave (CW) and pulsed illumination where multiple illumination beams are multiplexed (e.g., a pulsed beam is multiplexed with a CW beam), permitting signal discrimination between a signal induced by the CW source and a signal induced by the pulsed source. For example, in some embodiments, LEDs (e.g., aluminum gallium arsenide red diodes, gallium phosphide green diodes, gallium arsenide phosphide green diodes, or indium gallium nitride violet/blue/ultraviolet (UV) diodes) are used as the pulsed illumination source. One commercially available example of a suitable UV LED excitation diode suitable for use in the present invention is Model NSHU55OE (Nichia Corporation), which emits 750 to 1000 microwatts of optical power at a forward current of 10 milliamps (3.5-3.9 volts) into a beam with a full-width at half maximum of 10 degrees, a peak wavelength of 370-375 nanometers, and a spectral half-width of 12 nanometers.

In some cases, the illumination source may provide diffuse illumination to the colorant. For example, an array of multiple point light sources (e.g., LEDs) may simply be employed to provide relatively diffuse illumination. Another particularly desired illumination source that is capable of providing diffuse illumination in a relatively inexpensive manner is an electroluminescent (EL) device. An EL device is generally a capacitor structure that utilizes a luminescent material (e.g., phosphor particles) sandwiched between electrodes, at least one of which is transparent to allow light to escape. Application of a voltage across the electrodes generates a changing electric field within the luminescent material that causes it to emit light.

The detector may generally be any device known in the art that is capable of sensing a signal. For instance, the detector may be an electronic imaging detector that is configured for spatial discrimination. Some examples of such electronic imaging sensors include high speed, linear charge-coupled devices (CCD), charge-injection devices (CID), complementary-metal-oxide-semiconductor (CMOS) devices, and so forth. Such image detectors, for instance, are generally two-dimensional arrays of electronic light sensors, although linear imaging detectors (e.g., linear CCD detectors) that include a single line of detector pixels or light sensors, such as, for example, those used for scanning images, may also be used. Each array includes a set of known, unique positions that may be referred to as "addresses." Each address in an image detector is occupied by a sensor that covers an area (e.g., an area typically shaped as a box or a rectangle). This area is generally referred to as a "pixel" or pixel area. A detector pixel, for instance, may be a CCD, CID, or a CMOS sensor, or any other device or sensor that detects or measures light. The size of detector pixels may vary widely, and may in some cases have a diameter or length as low as 0.2 micrometers.

In other embodiments, the detector may be a light sensor that lacks spatial discrimination capabilities. For instance, examples of such light sensors may include photomultiplier devices, photodiodes, such as avalanche photodiodes or silicon photodiodes, and so forth. Silicon photodiodes are sometimes advantageous in that they are inexpensive, sensitive, capable of high-speed operation (short risetime/high bandwidth), and easily integrated into most other semiconductor technology and monolithic circuitry. In addition, silicon photodiodes are physically small, which enables them to be readily incorporated into various types of detection systems. If silicon photodiodes are used, then the wavelength range of the emitted signal may be within their range of sensitivity, which is 400 to 1100 nanometers.

Optical readers may generally employ any known detection technique, including, for instance, luminescence (e.g., fluorescence, phosphorescence, etc.), absorbance (e.g., fluorescent or non-fluorescent), diffraction, etc. In one particular embodiment of the present, the optical reader measures color intensity as a function of absorbance. In one embodiment, absorbance readings are measured using a microplate reader from Dynex Technologies of Chantilly, Va. (Model # MRX). In another embodiment, absorbance readings are measured using a conventional test known as "CIELAB", which is discussed in *Pocket Guide to Digital Printing* by F. Cost, Delmar Publishers, Albany, N.Y. ISBN 0-8273-7592-1 at pages 144 and 145. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors. In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D18 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still another suitable optical reader is the reflectance spectrophotometer described in U.S. Patent App. Pub. No. 2003/0119202 to Kaylor, et al., which is incorporated herein in its entirety by reference thereto for all purposes. Likewise, transmission-mode detection systems may also be used in the present invention.

Figure 1B:
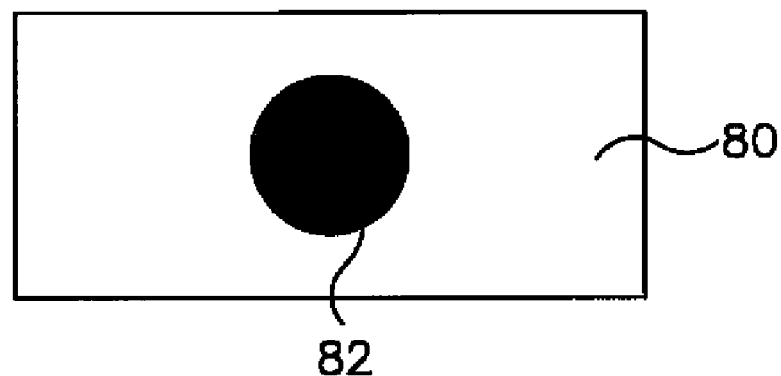

The above-described screening techniques may be implemented in a variety of ways in accordance with the present invention. For example, a solid support (e.g., wipe) may be utilized that contains a detection zone that provides any number of distinct detection regions (e.g., lines, dots, stripes, etc.) so that a user may better determine the presence of *Candida* or other microorganisms within a test sample. Each region may contain the same colorant, or may contain different colorants for reacting with different types of microorganisms. Referring to FIG. 1, one embodiment of the present invention is shown in which a solid support 80 is in the form of a wipe that employs a detection zone 82. For instance, the detection zone 82 may contain a colorant that undergoes a color change in the presence of *Candida albicans* (e.g., Phenol Red). When a dermal sample (e.g., skin) infected with *Candida albicans* contacts the wipe 80, the detection zone 82 undergoes a color change (FIG. 1B). However, when a dermal sample infected only with another microorganism (e.g., *S. aureus*) contacts the wipe 80, the detection zone 82 will remain substantially the same.

Although not required, an array of different colorants may also be employed to enhance the ability to differentiate *Candida* from other microorganisms. The array provides a distinct spectral response (e.g., pattern of colors) or "fingerprint" for *Candida*. For example, the array may provide a certain spectral response in the presence of *Candida albicans* or other *Candida* species, but provide a completely different spectral response in the presence of *S. aureus, E. coli*, or other bacteria commonly associated with diaper rash. Detection of the spectral response provided by the array may thus allow for enhanced differentiation *Candida* and other microorganisms.

When employed, the array may contain a plurality of discrete regions (referred to as "addresses") spaced apart in a predetermined pattern. The addresses contain a colorant capable of exhibiting a color change in the presence of a particular microorganism. The selection of colorants for the array is not critical to the present invention so long as the array produces a distinct spectral response. The individual array addresses may be configured in a variety of ways to accomplish this purpose. In one particular embodiment, individual array addresses may contain colorants that each exhibits a distinct spectral response in the presence of Candida and another microorganism (e.g., S. aureus or E. coli). For instance, a first array address may contain a phthalein colorant (e.g., Phenol Red) and a second array address may contain a N-phenolate betaine colorant (e.g., Reichardt's dye). Of course, the spectral distinction between individual array addresses need not always be provided by the use of different colorants. For example, the same colorants may be used in individual array addresses, but at a different concentration so as to produce a different spectral response. Certain addresses may likewise contain the same colorant at the same concentration, so long as the array as whole is capable of producing a distinct spectral response.

Apart from the composition of the individual array addresses, a variety of other aspects of the array may be selectively controlled to enhance its ability to provide a distinct spectral response. One factor that influences the ability of the array to produce a distinct spectral response is the number of array addresses employed. Namely, a greater number of individual array addresses may enhance the degree that the spectral response varies for different microorganisms. However, an overly large number of addresses can also lead to difficulty in visually differentiating between spectral responses. Thus, in most embodiments of the present invention, the array contains from 2 to 50 array addresses, in some embodiments from 3 to about 40 array addresses, and in some embodiments, from 4 to 20 array addresses. The number of addresses employed in the array will ultimately depend, at least in part, on the nature of the selected colorants. That is, if the selected colorants have a similar color change in the presence of a microorganism, a larger number of addresses may be needed to provide the desired spectral response.

Another aspect of the array that may influence its ability to provide a distinctive spectral response is the pattern (e.g., size, spacing, alignment, etc.) of the individual array addresses. The individual array addresses may possess a size effective to permit visual observation without unduly increasing the size of the solid support. The size of the addresses may, for example, range from about 0.01 to about 100 millimeters, in some embodiments from about 0.1 to about 50 millimeters, and in some embodiments, from about 1 to about 20 millimeters. The shape of the addresses may also enhance visual observation of the spectral response. For example, the addresses may be in the form of stripes, bands, dots, or any other geometric shape. The addresses may also be spaced apart a certain distance to provide a more visible spectral response. The spacing between two or more individual array addresses may, for example, range from about 0.01 to about 100 millimeters, in some embodiments from about 0.1 to about 50 millimeters, and in some embodiments, from about 1 to about 20 millimeters. The overall pattern of the array may take on virtually any desired appearance.

Figure 2A:
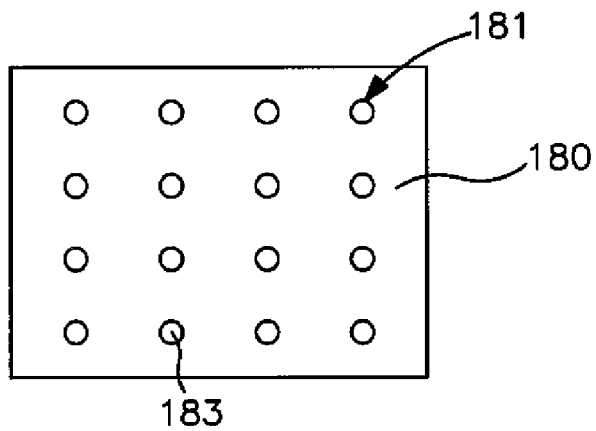
FIG. 2 is a perspective view of another exemplary wipe of the present invention before contact with a dermal sample (FIG. 2A); after contact with a sample infected with *Candida albicans* (FIG. 2B); and after contact with a sample infected with *S. aureus* or *E. coli* (FIG. 2C).
Figure 2B:
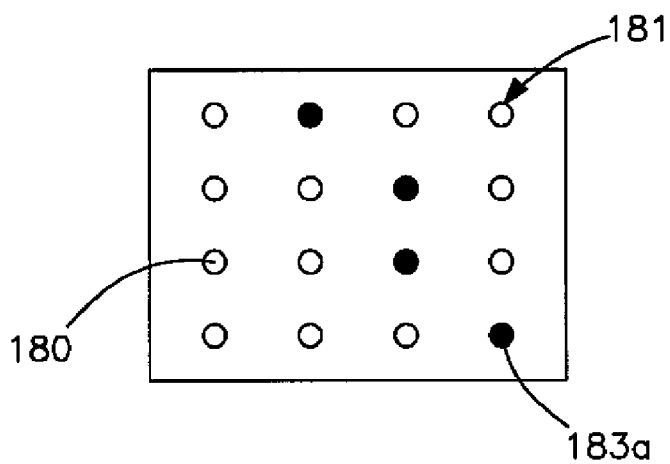
Figure 2C:
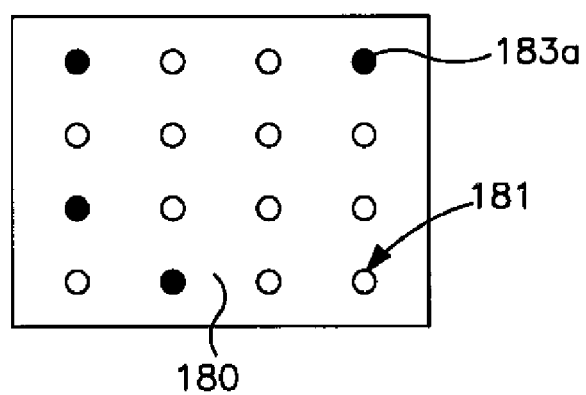

Referring to FIG. 2A, one embodiment of the present invention is shown in which a solid support 180 is in the form of a wipe that employs an array 181 containing a plurality of addresses 183, each of which includes a colorant. For example, a set of first addresses 183a may include colorants that undergo a color change in the presence of Candida albicans (e.g., Phenol Red) and a set of second addresses 183b may include colorants that undergo a color change in the presence of S. aureus or E. coli (e.g., Reichardt's dye). When a dermal sample (e.g., skin) infected with Candida albicans contacts the wipe 180, the first set of addresses 183a undergo a color change, while the second set of addresses 183b remains substantially the same or undergo only a faint color change (FIG. 2B). When a dermal sample infected with S. aureus or E. coli contacts the wipe 180, the second set of addresses 183b undergo a color change, while the first set of addresses 183a remains substantially the same or undergo only a faint color change (FIG. 2C).

Regardless, the spectral response of the colorant(s) may provide information about the presence of Candida or other microorganism to which it is exposed. If desired, the response of the test colorant(s) (or array of colorants) may be compared to a control colorant (or array of colorants) formed in a manner that is the same or similar to the test colorant(s) with respect to microorganism responsiveness. The comparison may be made visually or with the aid of an instrument. Multiple control colorants may likewise be employed that correspond to different types of microorganisms at a certain concentration. Upon comparison, the microorganism may be identified by selecting the control colorant having a spectral response that is the same or substantially similar to the response of the test colorant, and then correlating the selected control to a particular microorganism or class of microorganisms.

As a result of the present invention, it has been discovered that the presence of Candida or other microorganism may be readily detected through the use of a colorant that undergoes a detectable color change. The color change is rapid and may be detected within a relatively short period of time. For example, the change may occur in about 20 minutes or less, in some embodiments about 10 minutes or less, in some embodiments about 5 minutes or less, in some embodiments about 3 minutes or less, and in some embodiments, from about 10 seconds to about 2 minutes. In this manner, the colorant may provide a "real-time" indication of the presence or absence of Candida or other microorganism. Such a "real time" indication may alert a user or caregiver to apply a treatment composition (e.g., anti-fungal) to the infected area and/or to seek the advice of a medical professional. On the other hand, the lack of a color change may provide the user or caregiver with an assurance that the area is free of infection and sufficiently cleaned.

The present invention may be better understood with reference to the following examples.

EXAMPLES

Materials Employed

All reagents and solvents were obtained from Sigma-Aldrich Chemical Company, Inc. of St. Louis, Mo. unless otherwise noted and were used without further purification. The microorganisms used in the study were:

1. Gram Negative (Viable)
   Escherichia coli (ATCC #8739) (E. coli)
   Psuedomonas aeruginosa (ATCC #9027) (P. aeruginosa)
   Klebsiella pneumoniae (ATCC #4352) (K. pneumoniae)
   Proteus mirabilis (ATCC #7002) (P. mirabilis)
2. Gram Positive (Viable)
   Staphylococcus aureus (ATCC #6538) (S. aureus)
   Lactobacillus acidophilus (ATCC #11975) (L. acidophilus)

*Staphylococcus epidermidis* (ATCC #12228) (*S. epidermidis*)
*Bacillus subtilis* (ATCC #19659) (*B. subtills*)
*Enterococcus faecalis* (ATCC #29212) (*E. faecalis*)

3. Yeast (Viable)

*Candida albicans* (ATCC #10231) (*C. albicans*)

The colorants used in the study are listed with their molecular structure in Table 1:

TABLE 1

Exemplary Colorants and Their Corresponding Structure

| Colorant | Structure |
| --- | --- |
| 4-[(1-Methyl-4(1H)-pyridinylidene)ethylidene]-2,5-cyclohexadien-1-one hydrate | (structure shown) ·xH$_2$O |
| 3-Ethyl-2-(2-hydroxy-1-propenyl)benzothiazolium chloride | (structure shown) Cl$^-$ |
| 1-Docosyl-4-(4-hydroxystyryl)-pyridinium bromide | (structure shown) Br$^-$ |
| N,N-Dimethylindoaniline | (structure shown) |
| Quinalizarin | (structure shown) |
| Merocyanine 540 | (structure shown) |

TABLE 1-continued

Exemplary Colorants and Their Corresponding Structure

| Colorant | Structure |
| --- | --- |
| Eriochrome Blue SE | 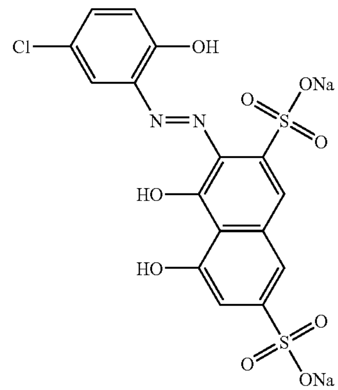 |
| Phenol Red | 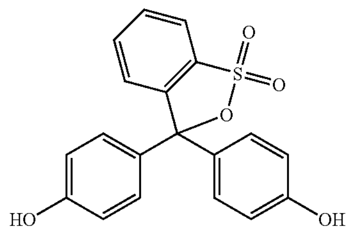 [SMILES: O=S1(=O)OC(c2ccc(O)cc2)(c2ccc(O)cc2)c2ccccc21] |
| Nile Blue A | 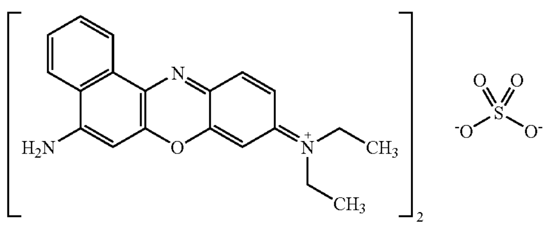 |
| 1-(4-Hydroxyphenyl)-2,4,6-triphenylpyridinium hydroxide inner salt hydrate | 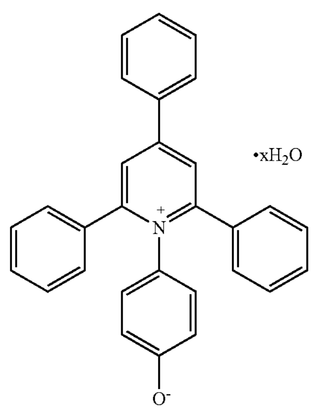 |
| Azomethine-H monosodium salt hydrate | 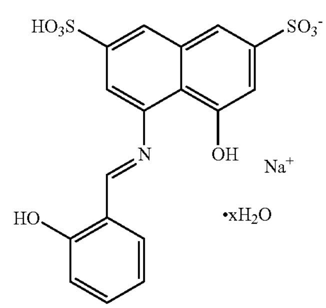 |

TABLE 1-continued
Exemplary Colorants and Their Corresponding Structure
| Colorant | Structure |
| --- | --- |
| Indingo carmine | 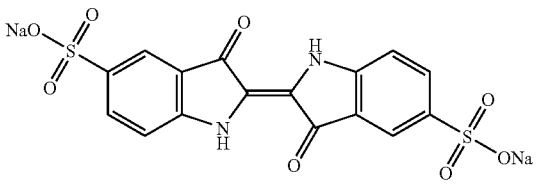 |
| Methylene Violet | 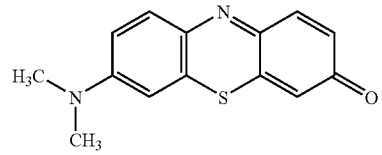 [SMILES: CN(C)c1ccc2nc3ccc(=O)cc-3sc2c1] |
| Eriochrome Blue Black B | 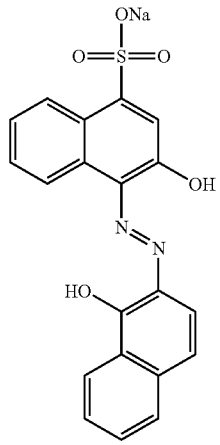 |
| Methylene Blue | 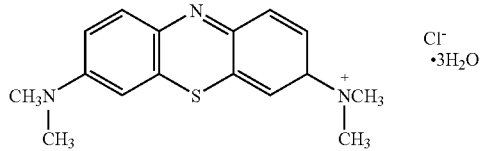 |
| Nile Red | 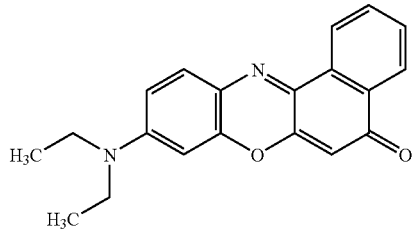 [SMILES: CCN(CC)c1ccc2nc3c4ccccc4c(=O)cc-3oc2c1] |
| Trypan Blue | 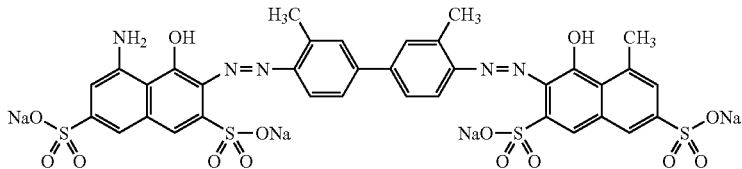 |

TABLE 1-continued

Exemplary Colorants and Their Corresponding Structure

| Colorant | Structure |
|---|---|
| Safranin O | 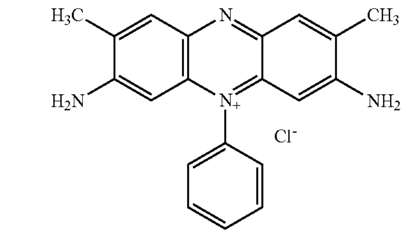 [SMILES: Cc1cc2nc3cc(C)c(N)cc3[n+](-c3ccccc3)c2cc1N ; [Cl-]] |
| Crystal Violet | 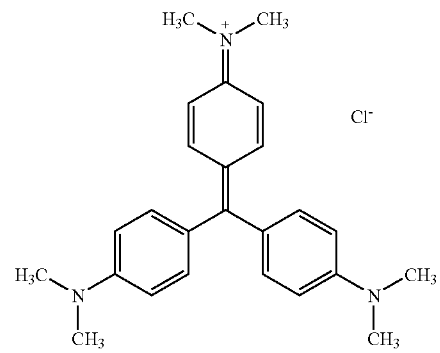 |
| Methyl Orange | 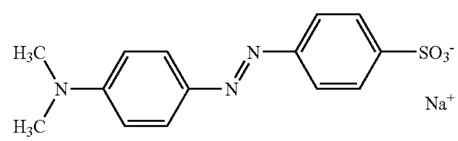 |
| Chrome Azurol S | 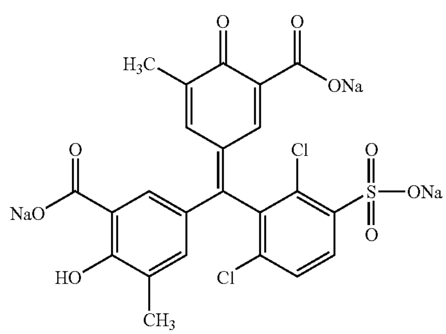 |
| Leucocrystal violet | 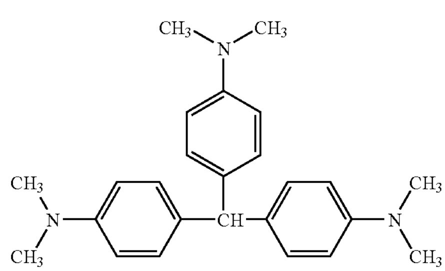 |
| Leucomalachite Green | 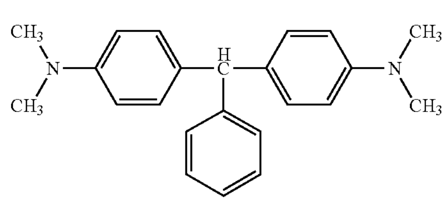 |

TABLE 1-continued
Exemplary Colorants and Their Corresponding Structure
| Colorant | Structure |
|---|---|
| Leuco xylene cyanole FF | 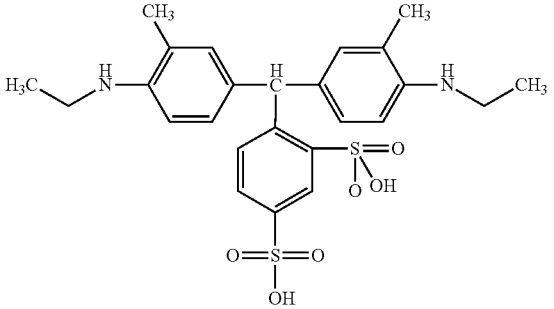 |
| 4,5-Dihydroxy-1,3-benzenedisulfonic acid disodium salt monohydrate | 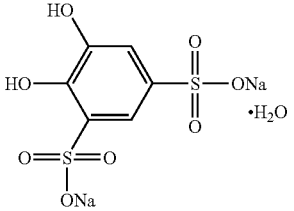 |
| 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt | 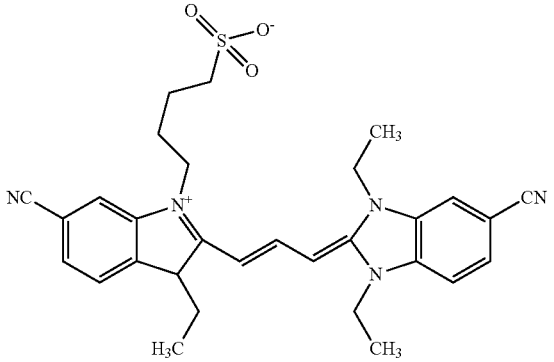 [SMILES: CCC1C(/C=C/C=C2/N(CC)c3ccc(C#N)cc3N2CC)=[N+](CCCCS(=O)(=O)[O-])c2cc(C#N)ccc21] |
| Acid Green 25 | 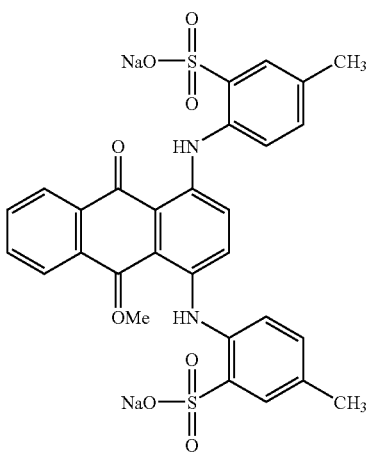 |

TABLE 1-continued

Exemplary Colorants and Their Corresponding Structure

| Colorant | Structure |
| --- | --- |
| Bathophenanthrolinedisulfonic acid disodium salt trihydrate | 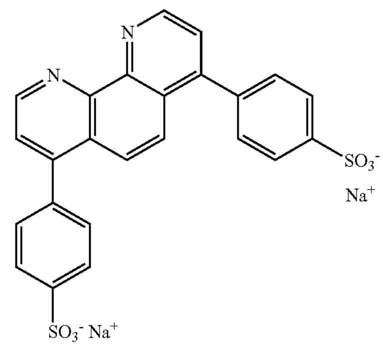 |
| Carminic Acid | 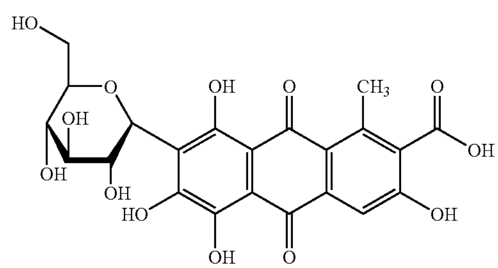 |
| Celestine Blue | 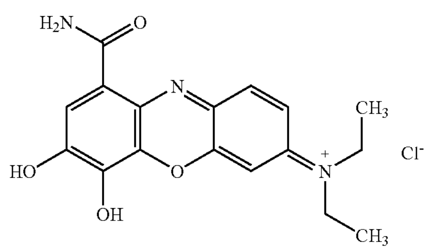 |
| Hematoxylin | 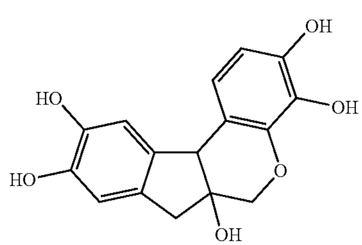 [SMILES: Oc1cc2c(cc1O)C1c3ccc(O)c(O)c3OCC1(O)C2] |
| Bromophenol Blue | 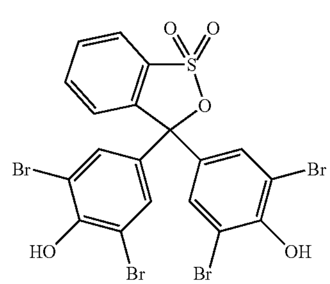 [SMILES: O=S1(=O)OC(c2cc(Br)c(O)c(Br)c2)(c2cc(Br)c(O)c(Br)c2)c2ccccc21] |

TABLE 1-continued
Exemplary Colorants and Their Corresponding Structure
| Colorant | Structure |
|---|---|
| Bromothymol blue | 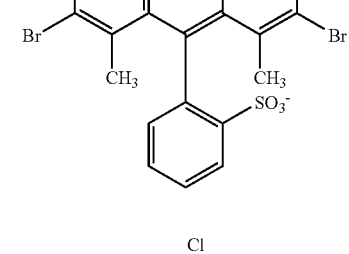 |
| Rose Bengal | 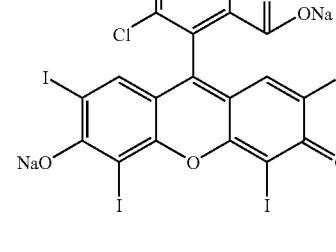 |
| Universal indicator 0-5 | Not available |
| Universal indicator 3-10 | Not available |
| Alizarin Complexone | 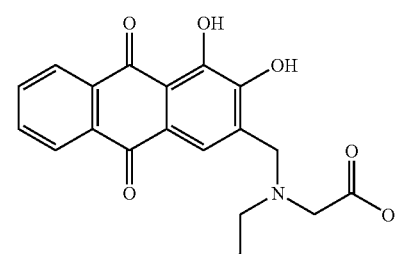 |
| Alizarin Red S | 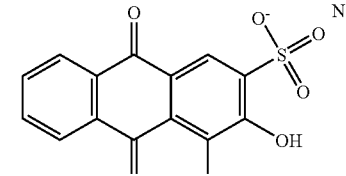 |
| Purpurin | 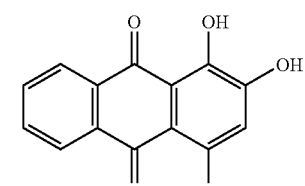 |

US 8,361,742 B2
TABLE 1-continued
Exemplary Colorants and Their Corresponding Structure
| Colorant | Structure |
|---|---|
| Alizarin | 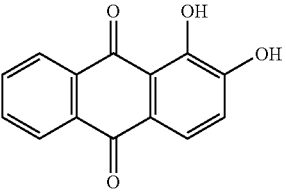 [SMILES: O=C1c2ccccc2C(=O)c2c1ccc(O)c2O] |
| Emodin | 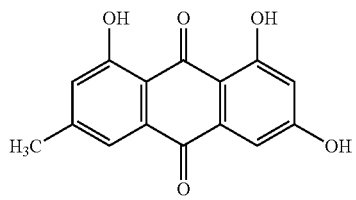 [SMILES: Cc1cc(O)c2c(c1)C(=O)c1cc(O)cc(O)c1C2=O] |
| Amino-4-hydroxyanthraquinone | 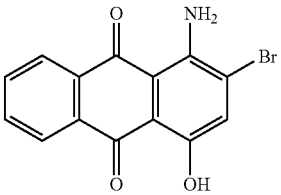 [SMILES: Nc1c(Br)cc(O)c2c1C(=O)c1ccccc1C2=O] |
| Nuclear Fast Red | 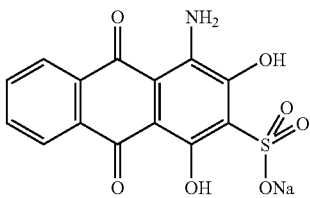 |
| Chlorophenol Red | 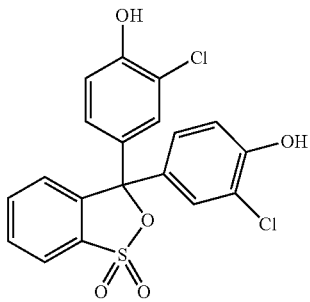 [SMILES: O=S1(=O)OC(c2ccc(O)c(Cl)c2)(c2ccc(O)c(Cl)c2)c2ccccc21] |
| Remazol Brilliant Blue R | 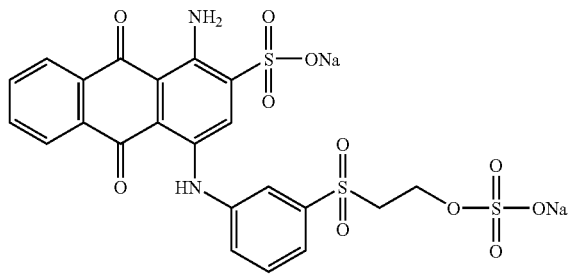 |

TABLE 1-continued

Exemplary Colorants and Their Corresponding Structure

| Colorant | Structure |
|---|---|
| Procion Blue HB | 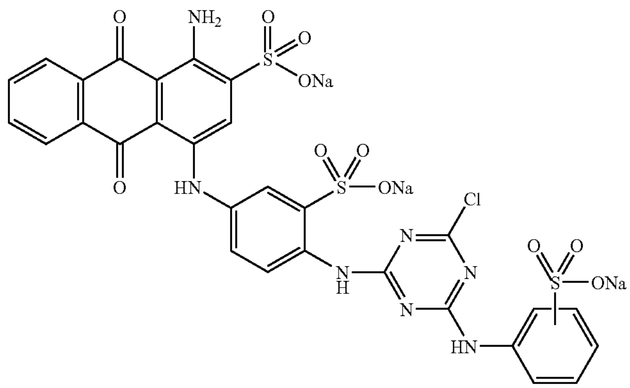 |
| Phenolphthalein | 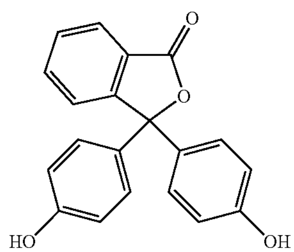 [SMILES: O=C1OC(c2ccc(O)cc2)(c2ccc(O)cc2)c2ccccc21] |
| Ninhydrin | 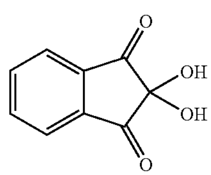 [SMILES: O=C1c2ccccc2C(=O)C1(O)O] |
| Nitro blue tetrazolium | 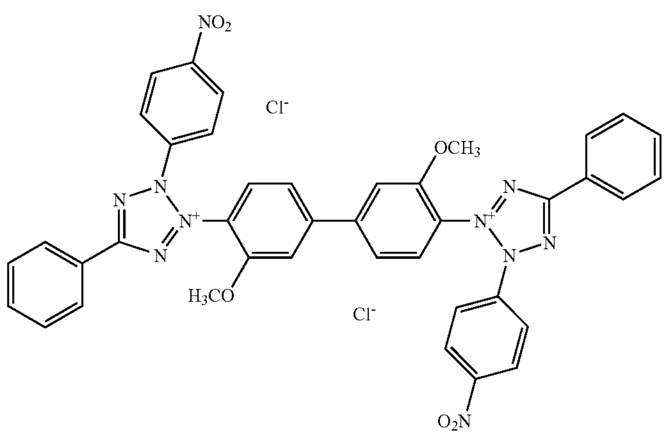 [SMILES: COc1cc(-c2ccc(-[n+]3nc(-c4ccccc4)nn3-c3ccc([N+](=O)[O-])cc3)c(OC)c2)ccc1-[n+]1nc(-c2ccccc2)nn1-c1ccc([N+](=O)[O-])cc1 ; [Cl-] ; [Cl-]] |
| Orcein | 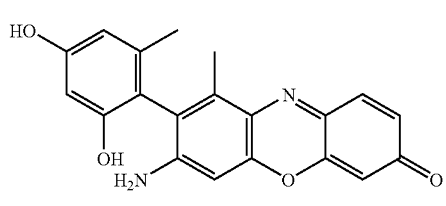 [SMILES: Cc1cc(O)cc(O)c1-c1c(N)cc2oc3cc(=O)ccc-3nc2c1C] |

TABLE 1-continued

Exemplary Colorants and Their Corresponding Structure

| Colorant | Structure |
|---|---|
| Celestine blue | 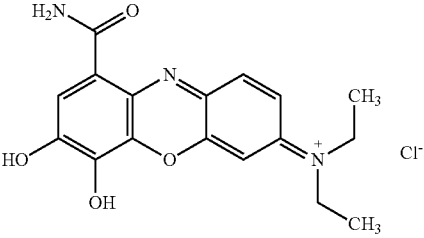 |
| Tetra Methyl-para-phenylene diamine (TMPD) | 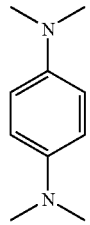 |
| 5,10,15,20-Tetrakis(pentafluorophenyl)-porphyrin iron(III) chloride | 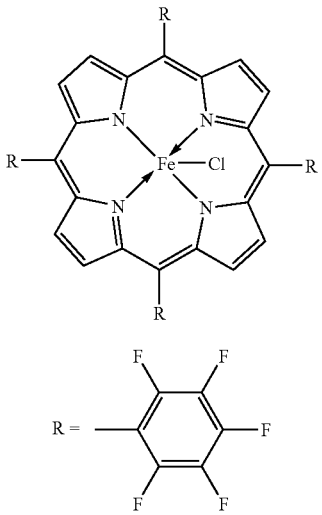 |

Example 1

Various colorants were tested for their ability to undergo a color change in the presence of S. aureus, E. coli, and C. albicans microorganisms. The colorants tested were Reichardt's dye, 1-Docosyl-4-(4-hydroxystyryl)pyridinium bromide, 3-Ethyl-2-(2-hydroxy-1-propenyl)-benzothiazolium chloride, 4-[(1-Methyl-4(1H)-pyridinylidene)ethylidene]-2,5-cyclohexadien-1-one hydrate, N,N-Dimethylindoaniline, Quinalizarin, Merocyanine 540, Eriochrome® Blue SE (Plasmocorinth B), Phenol Red, Nile Blue A, 1-(4-Hydroxyphenyl)-2,4,6-triphenylpyridinium hydroxide inner salt hydrate, Azomethine-H monosodium salt hydrate, Indigo Camine, Methylene Violet, Eriochrome® Blue Black B, Biebrich scarlet-acid fuchsin solution, Methylene Blue, Nile Red, Trypan Blue, Safranin O, Crystal Violet, Methyl Orange, and Chrome Azurol S.

Unless otherwise specified, the colorants were dissolved in dimethylformamide (DMF). The colorant solutions were then pipetted onto 15-cm filter paper (available from VWR International—Catalog No. 28306-153) and allowed to dry. The filter paper was sectioned into quadrants to test four (4) samples—i.e., S. aureus, E. coli, C. albicans, and sterile water. 100 microliters of $10^7$ CFU/mL of S. aureus was pipetted onto the filter paper in one quadrant, 100 microliters of $10^7$ CFU/mL of E. coli was pipetted onto the filter paper in a second quadrant, 100 microliters of $10^6$ CFU/mL of C. albicans was pipetted onto the filter paper in a third quadrant, and sterile water was pipetted in the final quadrant. Color changes in the colorants were observed and recorded for each of the samples tested. The color was recorded immediately after the color change to inhibit the fading (or loss of intensity) of the colors as the samples dried. Table 2 presents the observations from the experiment.

TABLE 2

Observations of Colorant Color Change (Group 1)

| Colorant | Initial Color | Color Change w/ S. aureus | Color Change w/ E. coli | Color Change w/ C. albicans | Color Change w/ sterile water |
|---|---|---|---|---|---|
| Reichardt's dye | Blue | Colorless | Colorless | Colorless | No change |
| 1-Docosyl-4-(4-hydroxystyryl)pyridinium bromide | Yellow | Very faint orange | Faint orange | Faint orange | Very faint orange |
| 3-Ethyl-2-(2-hydroxy-1-propenyl)benzothiazolium chloride, | White/cream | No change | No change | No change | No change |
| 4-[(1-Methyl-4(1H)-pyridinylidene)ethylidene]-2,5-cyclohexadien-1-one hydrate | Bright yellow | No change | No change | No change | No change |
| N,N-Dimethylindoaniline | Grey | Faint pink | Very faint pink | Very faint pink | No change |
| Quinalizarin | Peach | Yellow | Faint purple | Purple | No change |
| Merocyanine 540 | Hot pink | Light purple | Yellowish pink | Deeper yellowish pink | Reddish pink |
| Eriochrome Blue SE (Plasmocorinth B) | Deep pink | Very faint purple | Purple | Deep purple | Lighter pink with dark pink border (dissolution) |
| Phenol Red | Yellow | Yellow with orange border | Orange | Deep red/orange | Green with orange border |
| Nile Blue A | Blue | Pink | Pink | Pink | No change |
| 1-(4-Hydroxyphenyl)-2,4,6-triphenylpyridinium hydroxide inner salt hydrate | Yellow | No change | No change | No change | No change |
| Azomethine-H monosodium salt hydrate | Yellow/peach | Lighter with deeper border (dissolution) | Lighter with deeper border (dissolution) | Lighter with deeper border (dissolution) | Lighter with deeper border (dissolution) |
| Indigo Carmine | Light blue | Deeper light blue | Deeper light blue | Deeper light blue | Light blue with deeper border (dissolution) |
| Methylene Violet | Deep blue/violet | Deeper blue | Deeper blue | Deeper blue | No change |
| Eriochrome ® Blue Black B | Dark muddy purple | Lighter muddy purple | Deep purple | Deep blue | Darker muddy purple |
| Biebrich scarlet-acid fuchsin solution | Bright red | Lighter with deeper border (dissolution) | Lighter with deeper border (dissolution) | Lighter with deeper border (dissolution) | Lighter with deeper border (dissolution) |
| Methylene Blue* | Bright blue | No change | No change | No change | No change |
| Nile Red | Bright purple | Light pink | Light pink | Light pink | Faint pink |
| Trypan Blue* | Deep blue | No change | No change | No change | Faintly lighter with deeper border (dissolution) |
| Safranin O | Bright salmon | Yellowish with salmon edge | Yellowish with salmon edge | Yellowish with salmon edge | Pinkish with salmon edge |
| Crystal Violet | Deep blue | No change | No change | No change | Faintly lighter with deeper border (dissolution) |
| Methyl Orange | Bright orange | Yellow | Yellow | Yellow | Lighter orange with dark orange border (dissolution) |
| Chrome Azurol S | Pink | Light orange with dark orange border | Light yellow with dark pink border | Brighter yellow with dark pink border | Light pink with dark pink border |

*Dissolved in water

With the exception of Methyl Orange, Nile Red, and Merocyanine 540, the observed color change was almost immediate (1 to 2 minutes).

Example 2

Various colorants were tested for their ability to undergo a color change in the presence of *S. aureus*, *E. coli*, and *C. albicans* microorganisms. The colorants tested were Leucocrystal Violet, Leucomalachite Green, Leuco xylene cyanole FF, 4,5-Dihydroxy-1,3-benzenedisulfonic acid disodium salt monohydrate, 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt, Acid Green 25, Bathophenanthrolinedisulfonic acid disodium salt trihydrate, Carminic Acid, Celestine Blue, Hematoxylin, Bromophenol Blue, Bromothymol Blue, Rose Bengal, Universal Indicator (0-5), and Universal Indicator (3-10). Unless otherwise specified, the colorants were dissolved in dimethylformamide (DMF). The VWR filter paper and colorants were prepared as described in Example 1. Table 3 presents the observations from the experiment.

TABLE 3

Observations of Colorant Color Change (Group 2)

| Colorant | Initial Color | Color Change w/*S. aureus* | Color Change w/*E. coli* | Color Change w/*C. albicans* | Color Change w/sterile water |
| --- | --- | --- | --- | --- | --- |
| Leucocrystal violet | White | Blue | Blue | Blue | No change |
| Leucomalachite Green | White | Green | Green | Green | No change |
| Leuco xylene cyanole FF | White | No change | No change | No change | No change |
| 4,5-Dihydroxy-1,3-benzenedisulfonic acid disodium salt monohydrate* | White | No change | No change | No change | No change |
| 5-Cyano-2-[3-(5-cyano-1,3-diethyl-1,3-dihydro-2H-benzimidazol-2-ylidene)-1-propenyl]-1-ethyl-3-(4-sulfobutyl)-1H-benzimidazolium hydroxide inner salt | Bright reddish pink | Dark pink | Dark purplish pink | Dark greenish pink | Lighter pink with dark pink border (dissolution) |
| Acid Green 25 | Green | Lighter green with darker green border (dissolution) | Lighter green with darker green border (dissolution) | Lighter green with darker green border (dissolution) | Lighter green with darker green border (dissolution) |
| Bathophenanthrolinedisulfonic acid disodium salt trihydrate** | White | No change | No change | No change | No change |
| Carminic Acid* | Reddish peach | Pale purple | Purple | Dark purple | Lighter peach with darker peach border (dissolution) |
| Celestine Blue | Dark lavender | Blue | Blue | Blue | Blue |
| Hematoxylin | Pale yellow | No change | Light purple | Darker purple | Pale yellow with darker yellow border (dissolution) |
| Bromophenol Blue | Bright Yellow | Dark blue | Dark blue | Dark blue | Lighter yellow with orangeish border (dissolution) |
| Bromothymol Blue | Yellow | Lighter yellow with darker yellow border | Light green | Darker green | Very light yellow/whitish with darker yellow border |
| Rose Bengal | Hot pink | Darker pink | Purplish pink | Reddish pink | White with dark pink border (dissolution) |
| Universal Indicator (0-5) | Yellowish green | Yellowish blue | Yellowish blue | Yellowish blue | Lighter green with dark green border (dissolution) |
| Universal Indicator (3-10) | Peach | Pinkish peach | Orangeish yellow | Yellow | Dark peach |

*Dissolved in water
**Dissolved in DMF and water

With the exception of Leucocrystal Violet, Leucomalachite Green, and Leuco xylene cyanole FF, the observed color change was almost immediate (1 to 2 minutes).

Example 3

Various colorants were tested for their ability to undergo a color change in the presence of *S. aureus, E. coli*, and *C. albicans* microorganisms. The colorants tested were Alizarin Complexone, Alizarin Red S, Purpurin, Alizarin, Emodin, Amino-4-hydroxyanthraquinone, Nuclear Fast Red, Chlorophenol Red, Remazol Brilliant Blue R, Procion Blue HB, Phenolphthalein, tetraphenylporphine, tetra-o-sulphonic acid, and Ninhydrin. Unless otherwise specified, the colorants were dissolved in dimethylformamide (DMF). The VWR filter paper and colorants were prepared as described in Example 1. Table 4 presents the observations from the experiment.

TABLE 4

Observations of Colorant Color Change (Group 3)

| Colorant | Initial Color | Color Change w/*S. aureus* | Color Change w/*E. coli* | Color Change w/*C. albicans* | Color Change w/ sterile water |
|---|---|---|---|---|---|
| Alizarin Complexone | Yellow | Brown | Reddish purple | Purple | No change |
| Alizarin Red S | Yellow | Orangeish brown | Pinkish purple | Purple | Lighter yellow with darker yellow border (dissolution) |
| Purpurin | Peachish orange | Darker peachish orange | Reddish pink | Deeper reddish pink | Yellowish peach |
| Alizarin | Butter yellow | No change | Light brown | Purplish brown | Greenish butter yellow |
| Emodin | Yellow | No change | Faint Greenish orange | Deeper greenish orange | Greenish yellow |
| Amino-4-hydroxyanthraquinone | Pink | Lighter pink | Slightly lighter pink | Faintly lighter pink | Darker pink |
| Nuclear Fast Red | Reddish pink | Deeper reddish pink | Yellowish pink | Yellowish pink | Dark pink |
| Chlorophenol Red | Orangeish yellow | Brown | Deep reddish purple | Deeper reddish purple | Lighter orangeish yellow with darker border (dissolution) |
| Remazol Brilliant Blue R | Bright blue | Lighter blue with dark blue border (dissolution) | Lighter blue with dark blue border (dissolution) | Lighter blue with dark blue border (dissolution) | Lighter blue with dark blue border (dissolution) |
| Procion Blue HB | Teal green | No change | No change | Faintly darker teal | Lighter teal with darker border (dissolution) |
| Phenolphthalein | White | No change | No change | No change | No change |
| Tetraphenylporphine, tetra-o-sulphonic acid | Black | Grey with darker borders (dissolution) | Grey with darker borders (dissolution) | Grey with darker borders (dissolution) | Grey with darker borders (dissolution) |
| Ninhydrin | White | Deep purple | Deep purple | Slightly lighter deep | No change |

The observed color change was almost immediate (1 to 2 minutes).

Example 4

The ability to rapidly detect various gram-positive and gram-negative microorganisms utilizing the colorants of Examples 1-3 was demonstrated. Additional colorants were also tested, including Plasmocorinth B, Nitro Blue, Alizarin Complexone, Orcein, Tetra Methyl-para-phenylene diamine (TMPD), Nile Red, Eriochrome Blue Black B, Phenol Red, Alizarin Red S, Carminic Acid, Fe(III) $C_3$, Celestine Blue, Kovac's Reagent, Chrome Azurol S, Universal Indicator 3-10, Methyl Orange, Merocyanine 540, and Iron III Chloride Porphyrin. The gram-positive microorganisms tested were *S. aureus, L. acidophilus, S. epidermidis, B. subtilis*, and *E. faecalis*. The gram-negative microorganisms tested were *E. coli, P. aeruginosa, K. pneumoniae*, and *P. mirabilis*.

The colorant samples were prepared in a manner similar to Example 1. Unless otherwise specified, the colorants were dissolved in dimethylformamide (DMF). Each of the colorant solutions were pipetted onto two separate pieces of VWR filter paper and allowed to dry. One filter paper sample with the dried colorant was sectioned into five approximately equal sections to test the five gram-positive microorganisms. The other filter paper sample was sectioned into quadrants to test the four gram negative microorganisms. 100 microliters of $10^7$ CFU/mL of each microorganism sample was pipetted into their respective section of the sample of filter paper. Table 5 presents the observations from the gram positive microorganisms and Table 6 presents the observations from the gram negative microorganisms.

TABLE 5

Color Change Observations for Gram Positive Microorganisms

| Colorant | Initial Color | Color Change w/ *B. subtilis* | Color Change w/*S. aureus* | Color Change w/*S. epidermidis* | Color Change w/ *E. faecalis* | Color Change w/ *L. acidophilus* |
|---|---|---|---|---|---|---|
| Plasmocorinth B | Deep pink | Purplish pink | Very faint purplish pink | Deeper pink | Reddish pink | Deeper reddish pink |
| Nitro Blue Tetrazolium | Yellowish white | No change | No change | No change | No change | No change |
| Alizarin Complexone | Yellow | Brownish red | Lighter brownish red | Lighter brownish red | Lighter brownish red | Brownish yellow |
| Orcein | Muddy purple | Light purple | Lighter muddy purple | Darker muddy purple | Darker muddy purple | Darker muddy purple |
| Tetra Methyl-para-phenylene diamine (TMPD)* | Bright lavender | Colorless | Colorless | Not tested | Not tested | Colorless |
| Nile Red | Bright purple | Light pink | Light pink | Light pink | Light pink | Light pink |
| Eriochrome Blue Black B | Dark Muddy purple | Bluish purple | Lighter muddy purple | Darker muddy purple | Darker muddy purple | Darker muddy purple |
| Phenol Red | Yellow | Orange with yellowish center | Yellow with orange border | Yellow with orange border | Yellow with orange border | Greenish yellow with orange border |
| Alizarin Red S | Yellow | Brownish pink | Light brown | Light brown | Light brown | Light Greenish brown |
| Carminic Acid* | Reddish peach | Pale purple | Paler purple | Paler purple | Purplish peach | Yellowish peach |
| Fe(III)C₃ | White | No change | No change | Not tested | Not tested | No change |
| Celestine Blue | Dark lavender | Blue | Blue | Blue | Blue | Blue |
| Kovac's Reagent | Pale yellow | White with greenish center and yellow border | White with greenish center and yellow border | White with greenish center and yellow border | White with greenish center and yellow border | White with greenish center and brown border |
| Chrome Azurol S | Pink | Pale yellow with reddish border | Light orange with dark orange border | Light yellowish orange with dark orange border | Light orange with dark orange border | Light red with dark red border |
| Universal Indicator 3-10 | Peach | Lighter peach with yellow center | Lighter peach with yellow center | Lighter peach with yellow center | Lighter peach | Red |
| Methyl Orange | Bright orange | Yellow | Yellow | Yellow | Yellow | Yellow |
| Merocyanine 540 | Hot pink | Light purple | Light purple | Light purple | Light purple | Light purple |
| Iron III Chloride Porphyrin* | Light mustard yellow | Darker mustard yellow | Darker mustard yellow | Darker mustard yellow | Darker mustard yellow | Darker mustard yellow |

*Dissolved in water

TABLE 6

Color Change Observations for Gram Negative Microorganisms

| Colorant | Initial Color | Color Change w/ *E. coli* | Color Change w/*P. aeruginosa* | Color Change w/ *K. pneumoniae* | Color Change w/ *P. mirabilis* |
|---|---|---|---|---|---|
| Plasmocorinth B | Deep pink | Light purple | Deep blue | Deep reddish pink | Deep reddish pink |
| Nitro blue tetrazolium | Yellowish white | No change | No change | No change | No change |
| Alizarin Complexone | Yellow | Purple | Deeper purple | Brownish purple | Purple |
| Orcein | Muddy purple | Light purple | Dark purple | Brownish purple | Darker brownish purple |
| Tetra Methyl-para-phenylene diamine (TMPD)* | Bright lavender | Colorless | Dark purple | Colorless | Colorless |

TABLE 6-continued

Color Change Observations for Gram Negative Microorganisms

| Colorant | Initial Color | Color Change w/ E. coli | Color Change w/P. aeruginosa | Color Change w/ K. pneumoniae | Color Change w/ P. mirabilis |
|---|---|---|---|---|---|
| Nile Red | Bright purple | Light pink | Light pink | Light pink | Light pink |
| Eriochrome Blue Black B | Dark Muddy purple | Bluish purple | Dark blue | Darker purple | Darker purple |
| Phenol Red | Yellow | Orange | Dark red/orange | Yellow with orange border | Orange |
| Alizarin Red S | Yellow | Brownish purple | Deep reddish purple | Light brownish purple | Deep reddish purple |
| Carminic Acid* | Reddish peach | Blueish purple | Dark purple | Paler Bluish purple | Purple |
| $Fe(III)C_3$ | White | No change | No change | Not tested | No change |
| Celestine Blue | Dark lavender | Blue | Blue | Blue | Blue |
| Kovac's Reagent | Pale yellow | White with greenish center and yellow border | White with greenish center and yellow border | White with greenish center and yellow border | White with greenish center and yellow border |
| Chrome Azurol S | Pink | Greenish yellow with dark pink border | Bright yellow with dark pink border | Greenish yellow with dark pink border | Greenish yellow with dark pink border |
| Universal Indicator 3-10 | Peach | Lighter peach with yellow center | Light green | Darker peach with yellow center | Lighter peach with yellow center |
| Methyl Orange | Bright orange | Yellow | Yellow | Yellow | Orange/yellow |
| Merocyanine 540 | Hot pink | Yellowish pink | Yellowish pink | Yellowish pink | Yellowish pink |
| Iron III Chloride Porphyrin* | Mustard yellow | Darker mustard yellow | Darker mustard yellow | Darker mustard yellow | Darker mustard yellow |

*Dissolved in water

With the exception of Methyl Orange, Nile Red, Tetra Methyl-para-phenylene diamine (TMPD), and Merocyanine 540, the observed color change was also most immediate (1 to 2 minutes).

Example 5

Filter paper (available from VWR International) was treated with solutions of Chrome Azurol, Alizarin Complexone, Plasmocorinth B, and Phenol Red (all dissolved in DMF). The samples were hung dry to evaporate the solvent. Solutions of C. albicans, E. coli, and S. aureus were diluted in ten-fold dilutions using Trypticase Soybean Broth (TSB) media, and is some cases, sterile water, Concentrations ranged from $10^8$ CFU/mL (stock solution) down to $10^1$ CFU/mL for both E. coli and S. aureus, and $10^7$ CFU/mL (stock solution) down to $10^1$ CFU/mL for C. albicans. TSB and water were used as control solutions. 100 μL aliquots of each solution were applied to the samples. The color changes are summarized in Tables 7-11.

TABLE 7

Response to Dilutions of C. albicans in TSB media

| Dye | Initial Color | $10^6$ CFU/ml | $10^5$ CFU/ml | $10^4$ CFU/ml | $10^3$ CFU/ml | $10^2$ CFU/ml | $10^1$ CFU/ml | TSB Control |
|---|---|---|---|---|---|---|---|---|
| Phenol Red | Bright yellow | orange | Slightly darker orange | Slightly darker orange | Slightly darker orange | Slightly darker orange | Slightly darker orange | Dark orange |
| Plasmocorinth B | Bright pink | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Brownish purple | Slightly darker Brownish purple | Slightly darker Brownish purple | Slightly darker Brownish purple | Slightly darker Brownish purple | Slightly darker Brownish purple | Dark Brownish purple |
| Chrome Azurol | rose | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 8

Response to Dilutions of S. aureus in TSB media

| Dye | Initial Color | $10^8$ CFU/ml (undiluted) | $10^7$ CFU/ml | $10^6$ CFU/ml | $10^5$ CFU/ml | $10^4$ CFU/ml | $10^3$ CFU/ml | $10^2$ CFU/ml | TSB Control |
|---|---|---|---|---|---|---|---|---|---|
| Phenol Red | Bright yellow | Bright yellow | orange | Slightly darker orange | Slightly darker orange | Slightly darker orange | Slightly darker orange | Slightly darker orange | Dark orange |
| Plasmocorinth B | Bright pink | Bright purplish pink | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Light brown | Brownish purple | Slightly darker Brownish purple | Slightly darker Brownish purple | Slightly darker Brownish purple | Slightly darker Brownish purple | Slightly darker Brownish purple | dark Brownish purple |
| Chrome Azurol | rose | Brownish yellow | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 9

Response to Dilutions of S. aureus in water

| Dye | Initial Color | $10^7$ CFU/ml (in $H_2O$) | Water Control |
|---|---|---|---|
| Phenol Red | Bright yellow | N/A | Light yellow |
| Plasmocorinth B | Bright pink | Bright pink | Light pink |
| Alizarin Complexone | Bright yellow | Pale yellow | Pale yellow |
| Chrome Azurol | rose | Greenish red-pink | Light red-pink |

TABLE 10

Response to Dilutions of E. coli in TSB media

| Dye | Initial Color | $10^8$ CFU/ml (undiluted) | $10^7$ CFU/ml | $10^6$ CFU/ml | $10^5$ CFU/ml | $10^4$ CFU/ml | $10^3$ CFU/ml | $10^2$ CFU/ml | TSB Control |
|---|---|---|---|---|---|---|---|---|---|
| Phenol Red | Bright yellow | Light orange | orange | Slightly darker orange | Slightly darker orange | Slightly darker orange | Slightly darker orange | Slightly darker orange | Dark orange |
| Plasmocorinth B | Bright pink | Pinkish purple | Purplish blue | Slightly darker Purplish blue | Slightly darker Purplish blue | Slightly darker Purplish blue | Slightly darker Purplish blue | Slightly darker Purplish blue | Dark purplish blue |
| Alizarin Complexone | Bright yellow | Purplish brown | Brownish purple | Slightly darker Brownish purple | Slightly darker Brownish purple | Slightly darker Brownish purple | Slightly darker Brownish purple | Slightly darker Brownish purple | dark Brownish purple |
| Chrome Azurol | rose | Light green | Greenish yellow | Slightly darker Greenish yellow | Slightly darker Greenish yellow | Slightly darker Greenish yellow | Slightly darker Greenish yellow | Slightly darker Greenish yellow | Yellowish green |

TABLE 11

Response to Dilutions of E. coli in water

| Dye | Initial Color | $10^7$ CFU/ml (in $H_2O$) | Water Control |
|---|---|---|---|
| Phenol Red | Bright yellow | Orangish yellow | Light yellow |
| Plasmocorinth B | Bright pink | Bright pink | Light pink |
| Alizarin Complexone | Bright yellow | Brownish yellow | Pale yellow |
| Chrome Azurol | rose | Dark green | Light red-pink |

Thus, a color change was observed for the microorganisms that was different than the media alone, although the difference was somewhat more subtle for the dilute solutions. Without intending to be limited in theory, it is believed that the more subtle difference for the dilute solutions was due in part to the lack of time given to the microorganisms to condition the media (the experiment was conducted shortly after dilution). In contrast, the stock solutions contained microorganisms that had been in the media for 24 hours.

Example 6

Ink jet formulations including Phenol Red and Eriochrome Blue Black B were made according to the following recipe:

| Component | Wt. % |
|---|---|
| Ethylene Glycol | 6.0 |
| Glycerol | 3.0 |
| PEG 200 | 6.0 |
| 1,3-Propanediol | 3.0 |
| Surfynol ® 465 nonionic surfactant | 0.1 |
| Colorant + Water | 81.9 |

The formulations were filled into cartridges using standard methodologies. HUGGIES Supreme® scented baby wipes (basis weight of 75 grams per square meter) were printed with the inks using a Display Maker Series XII/62 color span printer. Exposure of the printed materials to $10^6$ CFU/mL of *C. albicans* resulted in a color change from yellow to bright orange for phenol red and from purple to dark blue for Eriochrome Blue Black B. Exposure to $10^7$ CFU/mL *E. coli* did not produce a noticeable color change with the ink jet printed materials.

Example 7

A formulation was made that included approximately 1 wt. % Phenol Red in water. The formulation was applied to a HUGGIES Supreme® scented baby wipe using a plastic dropper. The wipe was then exposed to various amounts of *C. albicans* (from $10^7$ to $10^3$ CFU/mL). A color change from yellow to orange was observable for each of the tested concentrations.

Example 8

A formulation was made that included approximately 1 wt. % Chlorophenol
Red in water. The formulation was applied to a HUGGIES Supreme® scented baby wipe using a plastic dropper. The wipe was then exposed to various amounts of *C. albicans* (from $10^7$ to $10^3$ CFU/mL). A color change from yellow to bright pink was observable for each of the tested concentrations.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wipe for detecting a secondary infection associated with diaper rash, the wipe comprising a phthalein compound that produces a first spectral response in the presence of *Candida albicans*, a second spectral response in the presence of *Staphylococcus aureus*, and a third spectral response in the presence of *Escherichia coil*, wherein the first spectral response is visually distinctive from the second and third spectral responses, wherein the wipe contains a nonwoven web and wherein the nonwoven web contains absorbent fibers, synthetic thermoplastic fibers, or a combination thereof.

2. The wipe of claim 1, wherein the phthalein compound undergoes a color change at a pH of about 6.6.

3. The wipe of claim 1, wherein the phthalein compound is Phenol Red.

4. The wipe of claim 1, wherein the first spectral response is produced at a *Candida albicans* concentration of about $1 \times 10^3$ or more colony forming units per milliliter.

5. The wipe of claim 1, wherein the first spectral response is produced at a *Candida albicans* concentration of about $1 \times 10^6$ or more colony forming units per milliliter.

6. The wipe of claim 1, wherein the wipe contains a wet wipe solution.

7. The wipe of claim 1, wherein the second spectral response is a color that is substantially the same as the color of the phthalein compound prior to contact with *Staphylococcus aureus*.

8. The wipe of claim 1, wherein the third spectral response is a color that is substantially the same as the color of the phthalein compound prior to contact with *Escherichia coll*.

9. The wipe of claim 1, wherein the phthalein compound is Phenol Red, Chlorophenol Red, Metacresol Purple, Cresol Red, Pyrocatecol Violet, Xylenol Blue, Xylenol Orange, Mordant Blue 3,3,4,5,6-tetrabromophenolsulfonephthalein, Bromoxylenol Blue, Bromophenol Blue, Bromochiorophenol Blue, Bromocresol Purple, Bromocresol Green, Bromothymol Blue, Thymol Blue, Bromocresol Purple, thymolphthalein, or a combination thereof.

* * * * *